United States Patent
Rodriguez et al.

(10) Patent No.: US 10,559,228 B2
(45) Date of Patent: Feb. 11, 2020

(54) PATIENT SIMULATOR AND ASSOCIATED DEVICES, SYSTEMS, AND METHODS

(71) Applicant: GAUMARD SCIENTIFIC COMPANY, INC., Miami, FL (US)

(72) Inventors: Alberto Rodriguez, Miami, FL (US); Victor Fernandez, Miami, FL (US); Yassel Valdes, Miami, FL (US); Lazaro Morales, Miami, FL (US)

(73) Assignee: Gaumard Scientific Company, Inc., Miami, FL (US)

( * ) Notice: Subject to any disclaimer, the term of this patent is extended or adjusted under 35 U.S.C. 154(b) by 190 days.

(21) Appl. No.: 15/880,720

(22) Filed: Jan. 26, 2018

(65) Prior Publication Data

US 2018/0218647 A1 Aug. 2, 2018

Related U.S. Application Data

(60) Provisional application No. 62/451,557, filed on Jan. 27, 2017.

(51) Int. Cl.
*G09B 23/28* (2006.01)
*G09B 23/30* (2006.01)
*A61M 16/00* (2006.01)

(52) U.S. Cl.
CPC ......... *G09B 23/303* (2013.01); *G09B 23/281* (2013.01); *G09B 23/288* (2013.01); *A61M 16/0003* (2014.02); *A61M 16/0057* (2013.01)

(58) Field of Classification Search
USPC .......................... 434/262, 265, 267, 268, 272
See application file for complete search history.

(56) References Cited

U.S. PATENT DOCUMENTS

| 4,167,070 | A |   | 9/1979  | Orden    |                         |
|-----------|---|---|---------|----------|-------------------------|
| 4,312,826 | A | * | 1/1982  | Colvin   | ........... B29C 33/3857 |
|           |   |   |         |          | 264/221                 |
| 5,584,701 | A | * | 12/1996 | Lampotang| ........... A61B 5/1106 |
|           |   |   |         |          | 434/262                 |
| 5,597,310 | A | * | 1/1997  | Edde     | ............. G09B 23/30 |
|           |   |   |         |          | 434/262                 |

(Continued)

OTHER PUBLICATIONS

International Search Report and Written Opinion dated Apr. 9, 2018 in related application PCT/US2018/015530, 10 pgs.

*Primary Examiner* — Kurt Fernstrom
(74) *Attorney, Agent, or Firm* — Haynes and Boone, LLP

(57) ABSTRACT

An apparatus and method according to which a patient simulator is used to simulate a human patient's breathing pattern, the patient simulator including a simulated respiratory system and a simulated airway system. The simulated respiratory system includes a lung valve, a simulated lung in communication with the lung valve, and a breathing pump including a cylinder and a piston dividing the cylinder into first and second chambers, the first chamber being in communication with the lung valve via at least a first flow path, and the second chamber being in communication with the lung valve via at least a second flow path. The simulated airway system is configured to be in communication with the second chamber of the breathing pump via at least a third flow path. In several exemplary embodiments, simulating, using the patient simulator, the human patient's breathing pattern comprises reciprocating the piston within the cylinder.

20 Claims, 38 Drawing Sheets

(56) References Cited

U.S. PATENT DOCUMENTS

| | | | | |
|---|---|---|---|---|
| 5,975,748 | A | 11/1999 | East, IV et al. | |
| 6,296,490 | B1 * | 10/2001 | Bowden | G09B 23/288 |
| | | | | 434/265 |
| 6,874,501 | B1 * | 4/2005 | Estetter | G09B 23/288 |
| | | | | 128/205.13 |
| 6,921,267 | B2 * | 7/2005 | van Oostrom | G09B 23/288 |
| | | | | 434/262 |
| 7,021,940 | B2 * | 4/2006 | Morris | G09B 23/28 |
| | | | | 434/267 |
| 8,500,452 | B2 | 8/2013 | Trotta et al. | |
| 8,517,740 | B2 * | 8/2013 | Trotta | G09B 23/281 |
| | | | | 434/267 |
| 2014/0315175 | A1 | 10/2014 | Nguyen et al. | |
| 2015/0079569 | A1 | 3/2015 | Rodriguez et al. | |

* cited by examiner

PATIENT SIMULATOR AND ASSOCIATED DEVICES, SYSTEMS, AND METHODS

CROSS-REFERENCE TO RELATED APPLICATION

This application claims the benefit of the filing date of, and priority to, U.S. patent application No. 62/451,557, filed Jan. 27, 2017, the entire disclosure of which is hereby incorporated herein by reference.

TECHNICAL FIELD

This disclosure is related in general to patient simulator systems for teaching patient care and, more particularly, to a simulated respiratory system for use with a patient simulator system in conducting patient care activity.

BACKGROUND

As medical science has progressed, it has become increasingly important to provide non-human interactive formats for teaching patient care. While it is desirable to train medical personnel in patient care protocols before allowing contact with real patients, textbooks and flash cards lack the important benefits to students that can be attained from hands-on practice. On the other hand, allowing inexperienced students to perform medical procedures on actual patients that would allow for the hands-on practice cannot be considered a viable alternative because of the inherent risk to the patient. Non-human interactive devices and systems can be used to teach the skills needed to successfully identify and treat various patient conditions without putting actual patients at risk.

For example, patient care education has often been taught using medical instruments to perform patient care activity on a physical simulator, such as a manikin—a manikin may be a life-sized anatomical human model used for educational and instructional purposes. Such training devices and systems can be used by medical personnel and medical students to teach and assess competencies such as patient care, medical knowledge, practice based learning and improvement, systems based practice, professionalism, and communication. The training devices and systems can also be used by patients to learn the proper way to perform self-examinations. However, existing simulators fail to exhibit accurate symptoms and to respond appropriately to student stimuli, thereby failing to provide realistic medical training to the students. Existing simulators also fail to look and feel lifelike, which fails to improve the training process. Thus, while existing physical simulators have been adequate in many respects, they have not been adequate in all respects. As such, there is a need to provide a simulator for use in conducting patient care training sessions that overcomes the above deficiencies of existing stimulators by, for example, being even more realistic and/or including additional simulated features.

DETAILED DESCRIPTION

Figure 1:
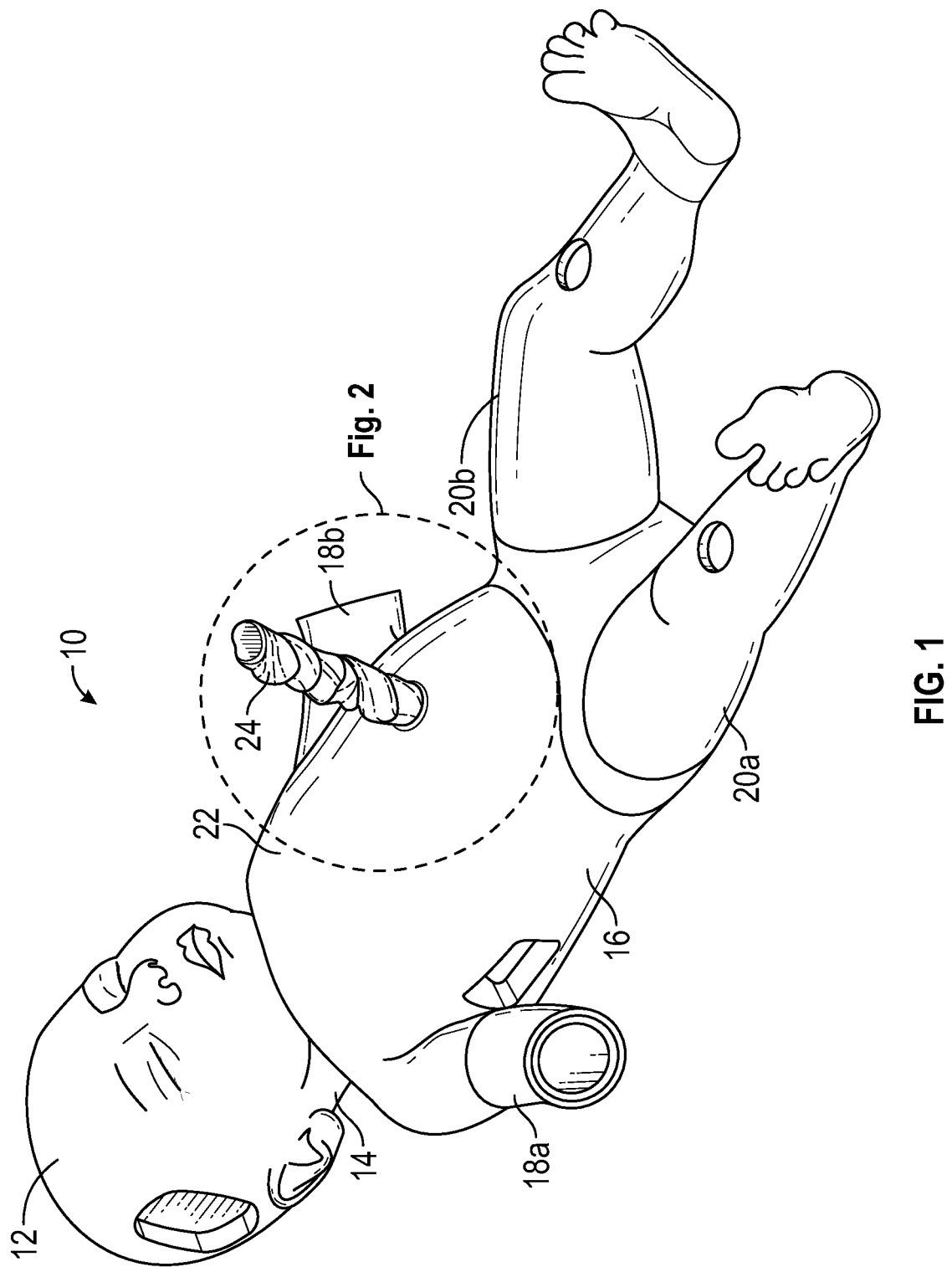
FIG. 1 is a perspective view of a patient simulator system including a simulated umbilicus, simulated arms, a simulated torso, simulated legs, and a simulated head, according to an exemplary embodiment.
Figure 2:
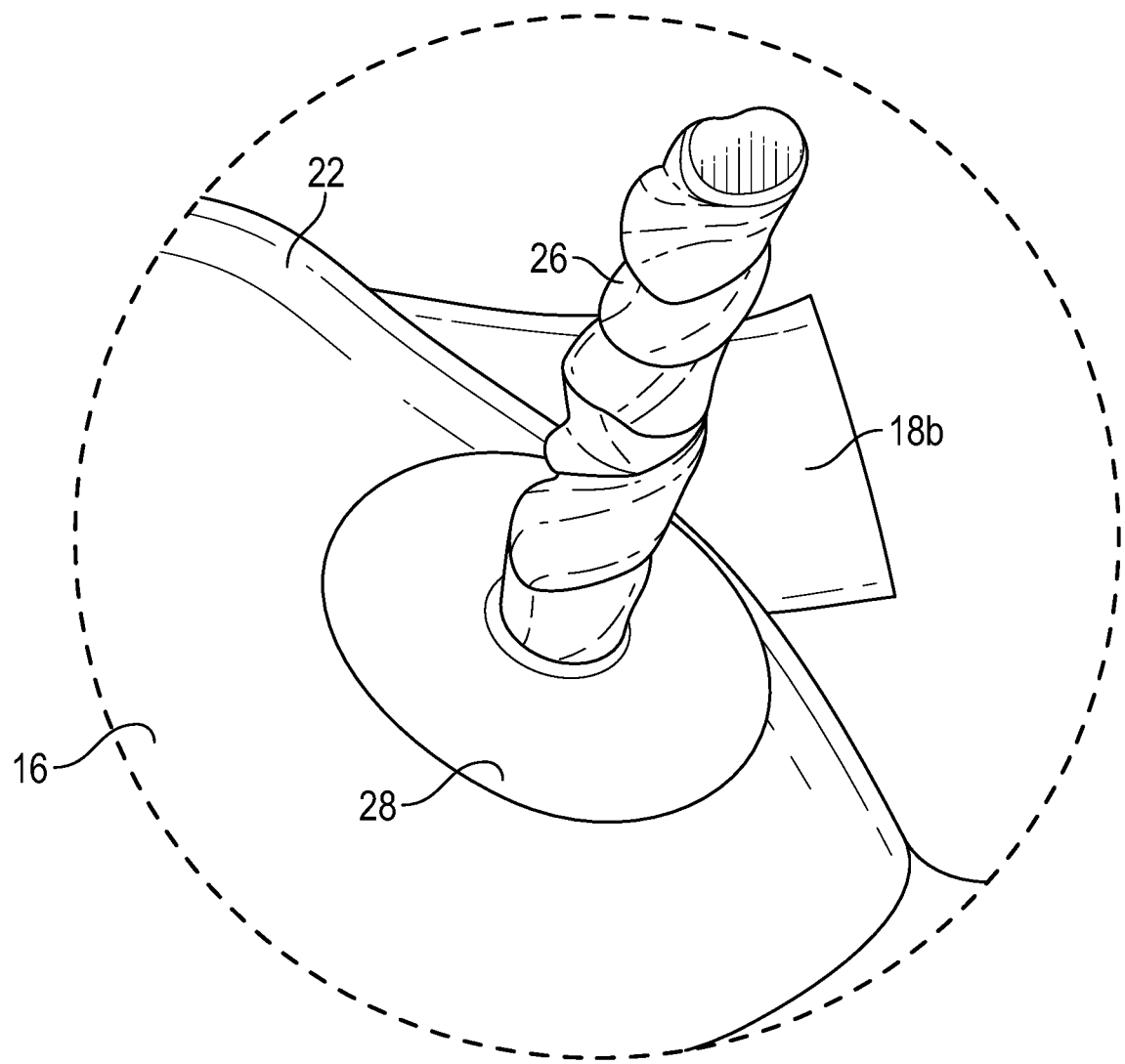
FIG. 2 is an enlarged view of the patient simulator system of FIG. 1, according to an exemplary embodiment.
Figure 3:
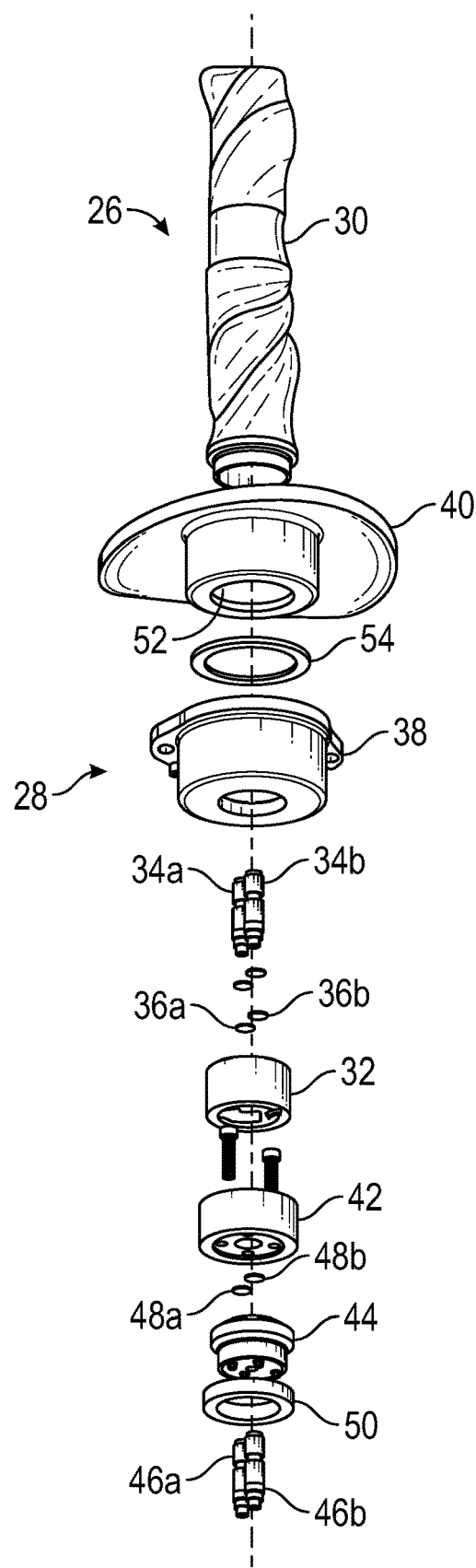
FIG. 3 is an exploded view of the simulated umbilicus of FIGS. 1 and 2, according to an exemplary embodiment.
Figure 4:
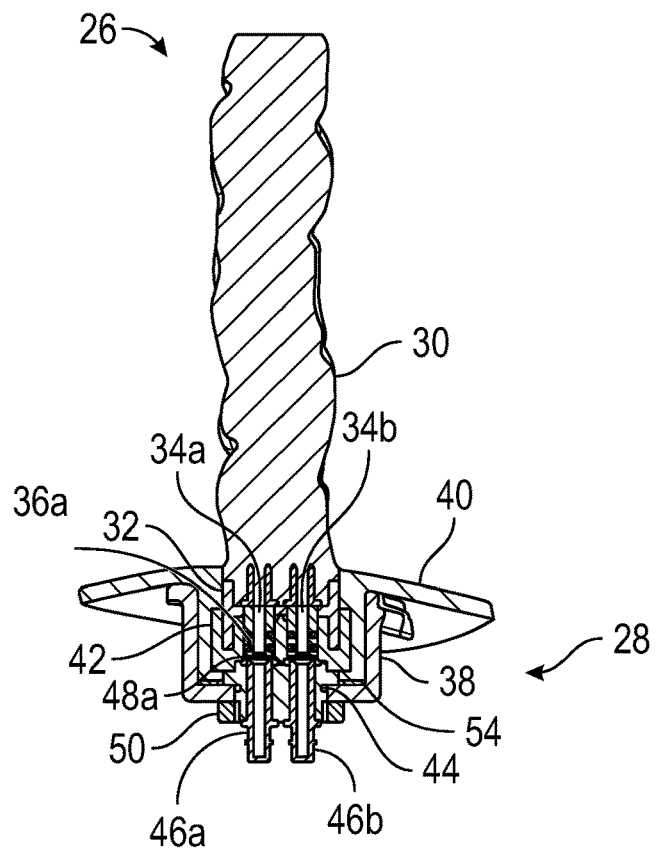
FIG. 4 is a cross-sectional view of the simulated umbilicus of FIGS. 1-3, according to an exemplary embodiment.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

One of the aims of healthcare simulation is to establish a teaching environment that closely mimics key clinical cases in a reproducible manner. The introduction of high fidelity tetherless simulators, such as those available from Gaumard Scientific Company, Inc., over the past few years has proven to be a significant advance in creating realistic teaching environments. The present disclosure is directed to a patient simulator system that expands the functionality of the simulators by increasing the realism of the look, feel, and functionality of the simulators that can be used to train medical personnel in a variety of clinical situations. The patient simulator systems disclosed herein offers a training platform on which team-building scenarios can be performed for the development of medical treatment skills and the advancement of patient safety.

In particular, the patient simulator system disclosed herein may be, include, or be part of a maternal patient simulator, an associated fetal patient simulator, and/or a newborn patient simulator that have improved realism and functionality compared to previously available simulators. Some of the various features that facilitate the improved realism and functionality are described in detail below. The patient simulator systems of the present disclosure allow users to practice a range of different simulated birthing and/or neonatal scenarios.

Thus, the patient simulator system facilitates the training of user's across the range of birthing and/or neonatal scenarios and corresponding assessment of the user's response to the different simulated birthing and/or neonatal scenarios. Accordingly, the user's medical treatment skills can be obtained and/or improved in a simulated environment without endangering a live patient.

Moreover, the patient simulator system allows for multiple users to simultaneously work with the patient simulator during a particular birthing and/or neonatal scenario, thereby facilitating team training and assessment in a realistic, team-based environment. By allowing multiple users to simultaneously interact with the patient simulator system, the system facilitates the real-time training and assessment of the cooperative efforts of an OB/GYN or pediatric team in a wide variety of birthing scenarios, neonatal scenarios, and/or patient safety scenarios, such as, by way of non-limiting example, a fire in the hospital. In some embodiments, the patient simulator system provides for pre-operative care simulation as well as post-operative care simulation, thereby allowing users to experience, address, and assess pre-operative and post-operative management, including pre-operative acquisition of the patient history and management of post-operative complications.

For example, in some embodiments, the patient simulator system allows for the realistic reception and transport of the patient simulator through a hospital (e.g., from an emergency room to an operating room) during operation of a particular birthing and/or neonatal scenario. In addition, the patient simulator systems can be used to conduct patient safety drills in an actual hospital or other medical setting.

In some embodiments, the patient simulator system includes features designed to enhance the educational experience. For example, in some embodiments, the system includes a processing module to simulate different medical and/or surgical scenarios during operation of the patient simulator system. In some embodiments, the system includes a camera system that allows visualization of the procedure for real-time video and log capture for debriefing purposes. In some embodiments, the patient simulator system is provided with a workbook of medical scenarios that are pre-programmed in an interactive software package, thereby providing a platform on which team-building scenarios can be performed for the development of medical treatment skills and general patient safety. Thus, the patient simulator system disclosed herein provides a system that is readily expandable and updatable without large expense and that enables users to learn comprehensive medical and surgical skills through "hands-on" training, without sacrificing the experience gained by users in using standard surgical instruments in a simulated patient treatment situation.

In an exemplary embodiment, as illustrated in FIGS. 1-5, a patient simulator system is generally referred to by the reference numeral 10. The patient simulator system 10 includes a simulated head 12, a simulated neck 14, a simulated torso 16, simulated arms 18a and 18b, simulated legs 20a and 20b, and simulated skin 22. A simulated umbilicus 24 is operably coupled to the simulated torso 16. The simulated umbilicus 24 includes an upper portion 26 and a closed-system base portion 28. In several exemplary embodiments, the upper portion 26 is detachably coupled to the closed-system base portion 28. The upper portion 26 includes a simulated umbilical cord 30, an umbilical cord plug 32, umbilical cord barb fittings 34a and 34b, and O-rings 36a and 36b. The O-rings 36a and 36b sealingly engage the exterior of the umbilical cord barb fittings 34a and 34b, which fittings are operably coupled to, and extend through, the umbilical cord plug 32. The umbilical cord plug 32 is also operably coupled to a lower end of the simulated umbilical cord 30. Moreover, encased within the simulated umbilical cord 30 is a y-shaped simulated umbilical artery (not shown) having upper ends positioned adjacent an upper end of the simulated umbilical cord 30, and a simulated umbilical vein (not shown) having an upper end positioned adjacent the upper end of the simulated umbilical cord 30. Respective lower ends of the simulated umbilical vein and the y-shaped simulated umbilical artery are connected to the umbilical cord barb fittings 34a and 34b.

The closed-system base portion 28 includes a receptacle 38, a skin layer 40, an upper umbilical plug receiver 42, a lower umbilical plug receiver 44, plug receiver barb fittings 46a and 46b, O-rings 48a and 48b, and a lock ring 50. The skin layer 40 inlays with the simulated skin 22 on the simulated torso 16, and defines a pocket 52 containing the upper umbilical plug receiver 42. The umbilical cord plug 32 is received by the upper umbilical plug receiver 42 so that the umbilical cord barb fittings 34a and 34b are operably coupled to, and extend through, the upper umbilical plug receiver 42. As a result, the O-rings 36a and 36b are sealingly engaged with the upper umbilical plug receiver 42. Moreover, the plug receiver barb fittings 46a and 46b are operably coupled to, and extend through, the lower umbilical plug receiver 44, which receiver engages both the upper umbilical plug receiver 42 and the skin layer 40 adjacent the pocket 52. As a result, the O-rings 48a and 48b are sealingly engaged between the plug receiver barb fittings 46a and 46b and the umbilical cord barb fittings 34a and 34b, respectively. In addition to, or instead of, being sealingly engaged between the plug receiver barb fittings 46a and 46b and the umbilical cord barb fittings 34a and 34b, respectively, the O-rings 48a and 48b may be sealingly engaged between the upper umbilical plug receiver 42 and the lower umbilical plug receiver 44. A portion of the skin layer 40 is engaged, and received, by the receptacle 38 so that a gasket 54 is disposed between, and sealingly engages, the receptacle 38 and the skin layer 40. Moreover, the lower umbilical plug receiver 44 is operably coupled to, and extends through, the receptacle 38 (vie the lock ring 50).

In several exemplary embodiments, one or both of the upper ends of the y-shaped simulated umbilical artery (not shown) may be used to perform a training procedure for an umbilical artery catheterization. To facilitate the training procedure for the umbilical artery catheterization, a simulated circulatory system (not shown) is operably coupled to the plug receiver barb fitting 46b, which fitting is operably coupled to the simulated umbilical artery via at least the umbilical cord barb fitting 34b. During the training procedure for the umbilical artery catheterization, the simulated circulatory system provides a pneumatic or hydraulic pulse to the simulated umbilical artery via at least the plug receiver barb fitting 46b and the umbilical cord barb fitting 34b.

Figure 5:
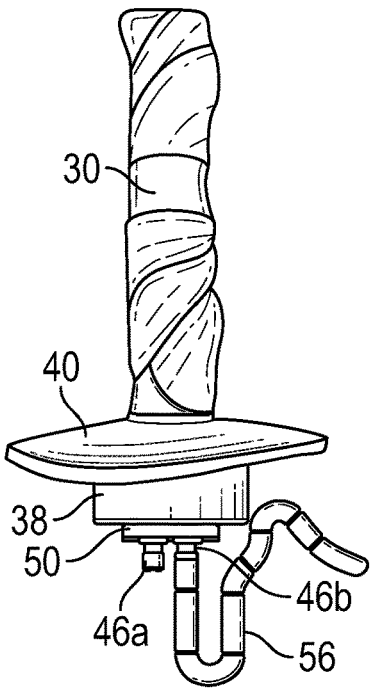
FIG. 5 is an elevational view of the simulated umbilicus of FIGS. 1-4, according to an exemplary embodiment.
Figure 6:
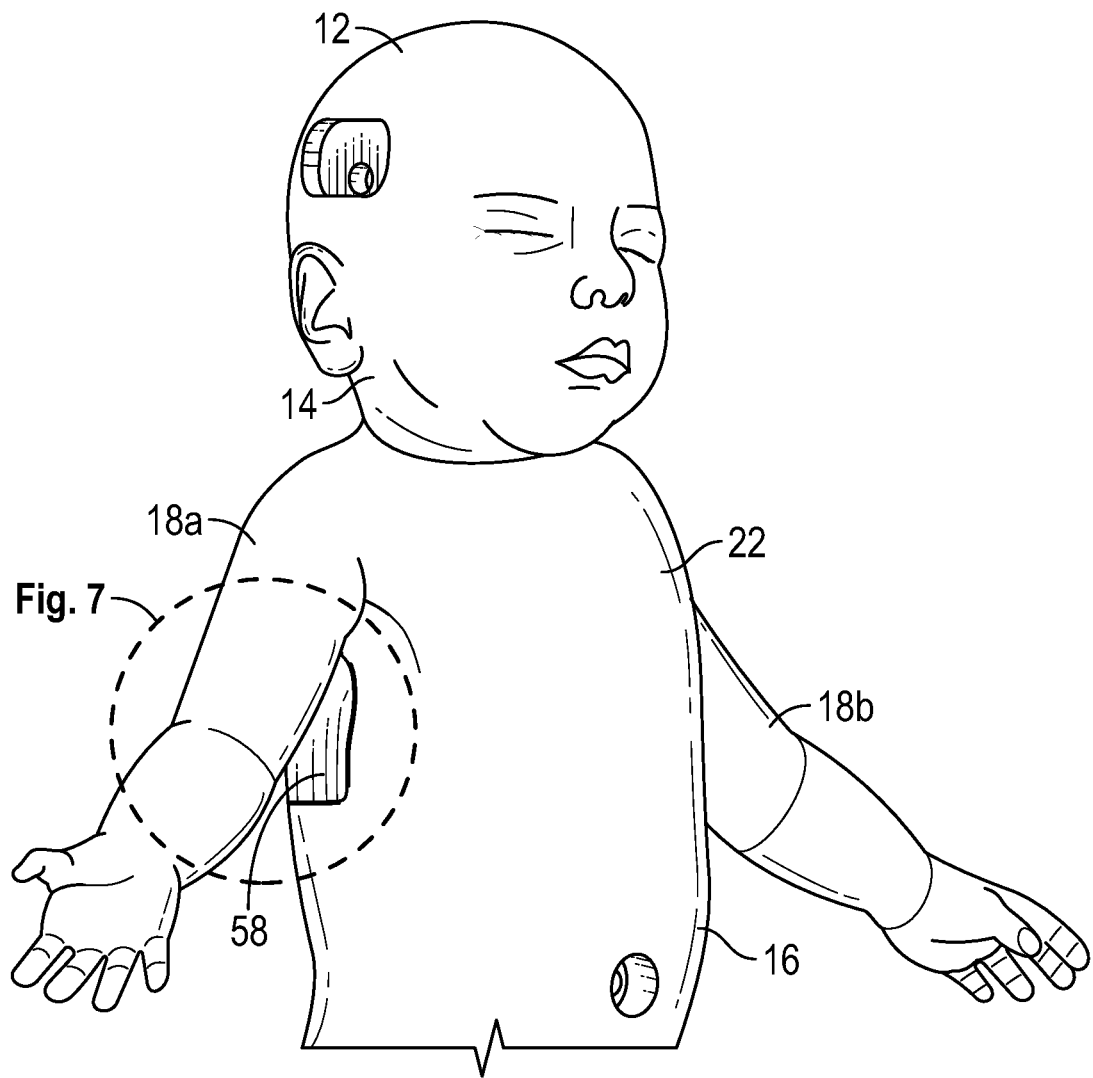
FIG. 6 is a perspective view of the patient simulator system of FIG. 1, the patient simulator system including a pneumothorax system, according to an exemplary embodiment.
Figure 7:
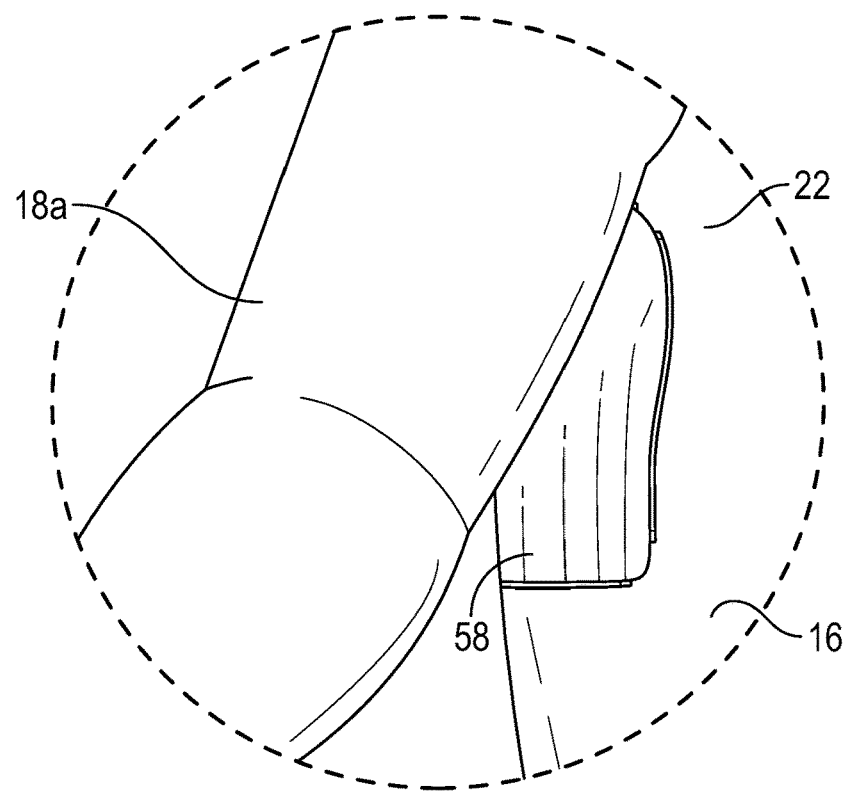
FIG. 7 is an enlarged view of the patient simulator system of FIG. 6, according to an exemplary embodiment.
Figure 8:
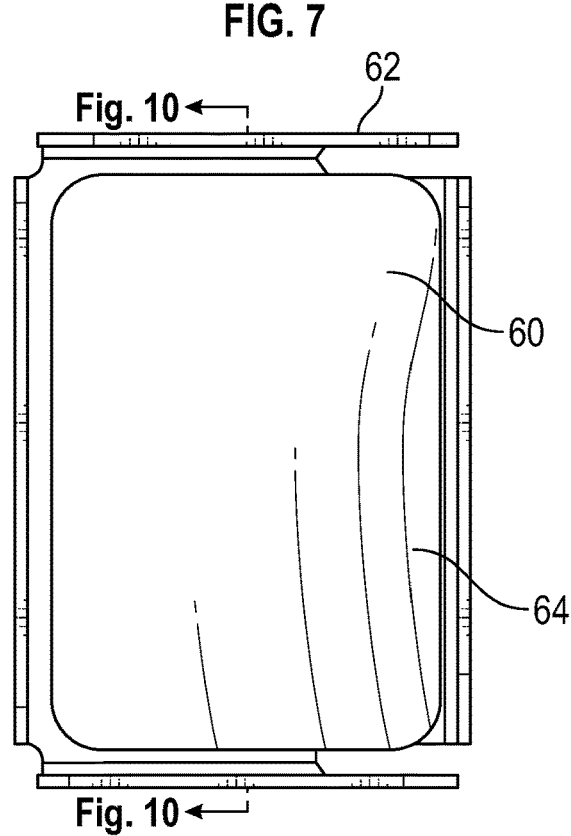
FIG. 8 is an elevational view of the pneumothorax system of FIGS. 6 and 7, the pneumothorax system including an insert and a cage, according to an exemplary embodiment.
Figure 9:
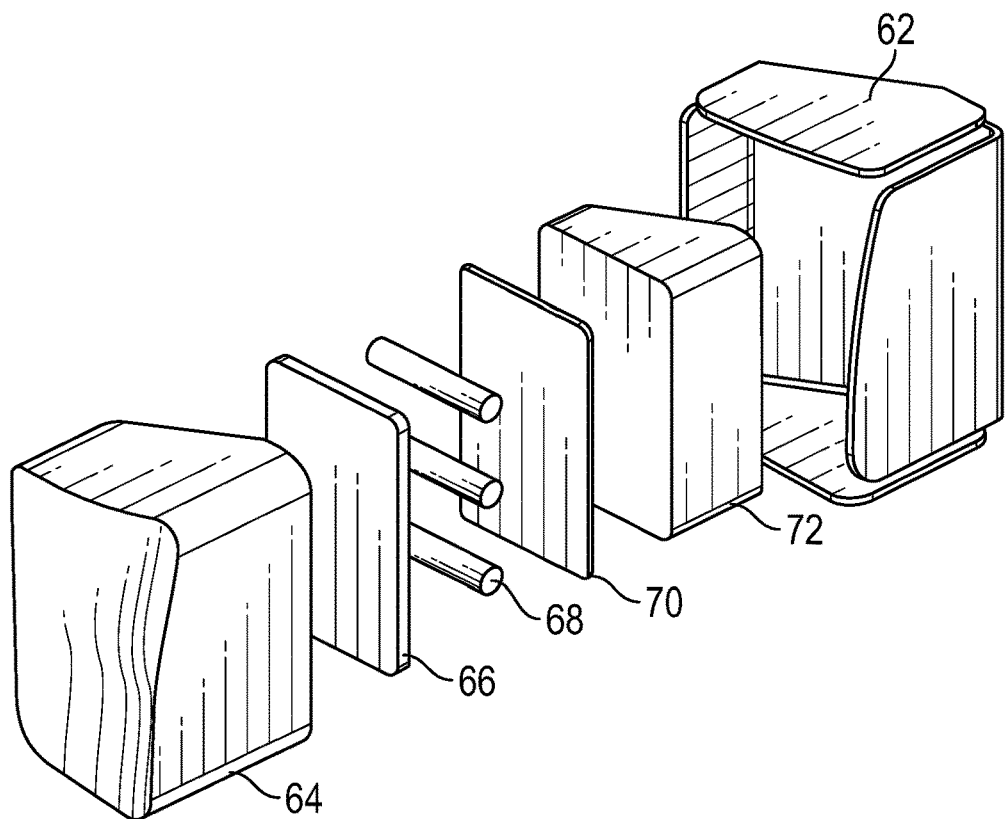
FIG. 9 is an exploded view of the pneumothorax system of FIGS. 6-8, according to an exemplary embodiment.
Figure 10:
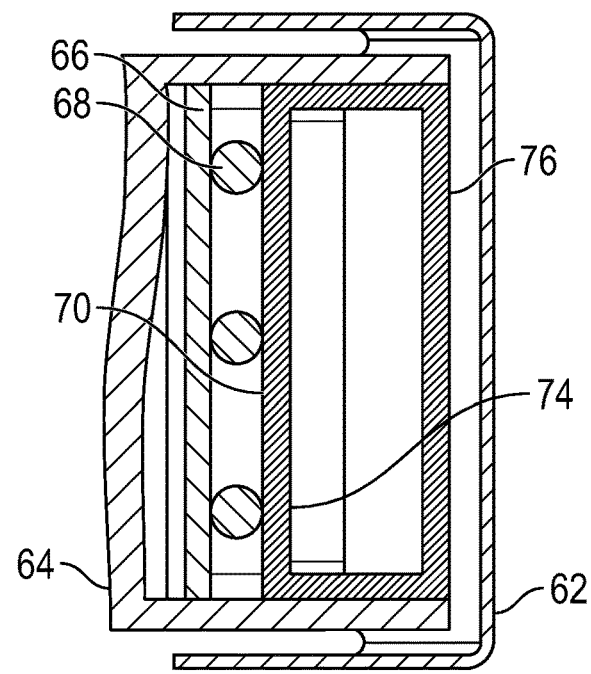
FIG. 10 is a cross-sectional view of the pneumothorax system of FIGS. 6-9, according to an exemplary embodiment.
Figure 11:
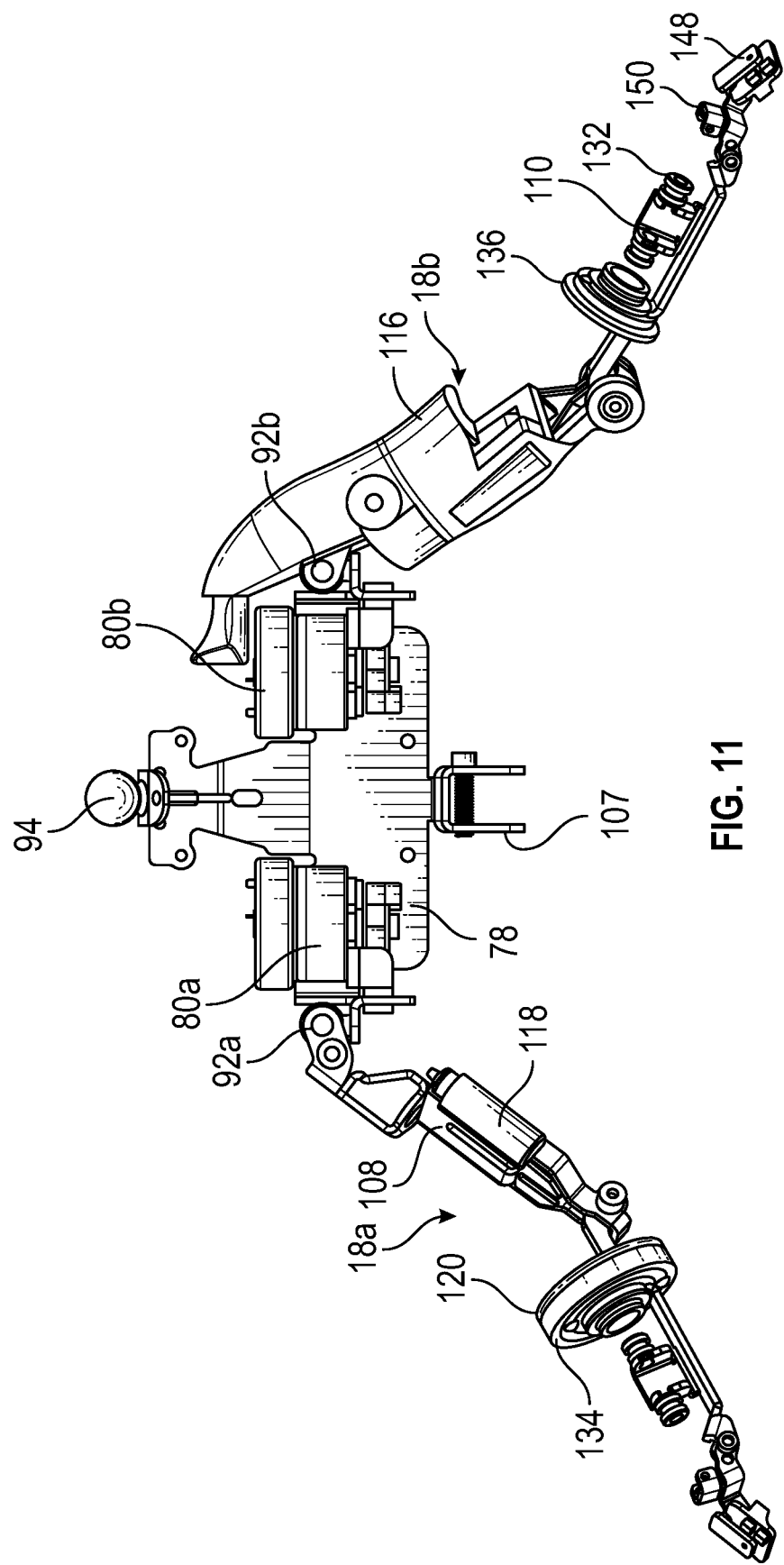
FIG. 11 is an elevational view of the simulated arms of FIG. 1 each connected to an upper torso bracket via an articulation joint, according to an exemplary embodiment.
Figure 12:
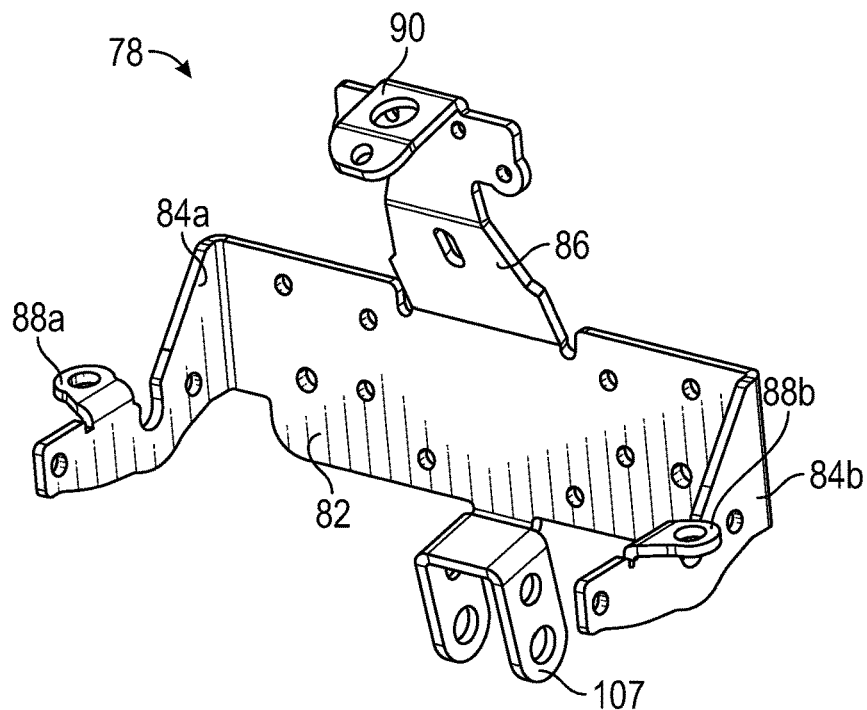
FIG. 12 is a perspective view of the upper torso bracket of FIG. 11, according to an exemplary embodiment.

In several exemplary embodiments, the upper end of the simulated umbilical vein (not shown) may be used to perform a training procedure for an umbilical vein catheterization. To facilitate the training procedure for the umbilical vein catheterization, a drainage line 56 is operably coupled to the plug receiver barb fitting 46a, which fitting is operably coupled to the simulated umbilical vein via at least the umbilical cord barb fitting 34a. As shown in FIG. 5, the drainage line 56 defines a unique geometry similar to that of a plumbing (sink) trap. This unique geometry allows pre-loading of fluid into the drainage line 56 for later use during the training procedure for the umbilical vein catheterization. More particularly, during the training procedure for the umbilical vein catheterization, the pre-loaded fluid may be removed from the drainage line 56 via the simulated umbilical vein, or additional fluid may be introduced into the drainage line 56 via the simulated umbilical vein. In the case where additional fluid is introduced into the drainage line 56 via the simulated umbilical vein, the pre-loaded fluid drains through the rear of the patient simulator system 10.

In several exemplary embodiments, fluid leakage during the training procedure for the umbilical artery catheterization and/or the training procedure for the umbilical vein catheterization is prevented, or at least reduced, by the sealing engagement of the O-rings 36a and 36b with the upper umbilical plug receiver 42, the sealing engagement of the O-rings 48a and 48b between the plug receiver barb fittings 46a and 46b and the umbilical cord barb fittings 34a and 34b, respectively, the sealing engagement of the O-rings 48a and 48b between the upper umbilical plug receiver 42 and the lower umbilical plug receiver 44, the sealing engagement of the gasket 54 between the receptacle 38 and the pocket 52, or any combination thereof.

In an exemplary embodiment, as illustrated in FIGS. 6-10, a pneumothorax system 58 is operably coupled to the simulated torso 16. The pneumothorax system 58 includes an insert 60 and a cage 62. In several exemplary embodiments, the insert 60 is detachably coupled to the cage 62. In several exemplary embodiments, the cage 62 is "floated" during the injection molding procedure to ensure proper orientation within the simulated skin 22 of the simulated torso 16. The insert 60 includes a skin layer 64, adipose tissue 66, ribs 68, endothoracic fascia 70, and a pleura cavity 72. In several exemplary embodiments, the skin layer 64 is, includes, or is part of, the simulated skin 22 of the patient simulator system 10. The skin layer 64 defines a pocket that receives the adipose tissue 66, the ribs 68, the endothoracic fascia 70, and the pleura cavity 72. More particularly, the adipose tissue 66, the ribs 68, and the endothoracic fascia 70 are sandwiched between the skin layer 64 and the pleura cavity 72, and the ribs 64 are sandwiched between the adipose tissue 66 and the endothoracic fascia 70. Moreover, the adipose tissue 66 engages the skin layer 64, and the endothoracic fascia 70 engages the pleural cavity 74. The pleura cavity 72 includes parietal pleura 74 and visceral pleura 76. In several exemplary embodiments, the pneumothorax system 58 bleeds when cut between the ribs 64 on the midaxillary line of the simulated torso 16, allowing drainage of fluid and escape of trapped air.

In an exemplary embodiment, as illustrated in FIGS. 11-21, the simulated arms 18a and 18b are operably coupled to an upper torso bracket 78. Also connected to the upper torso bracket 78 are arm motors 80a and 80b for actuating the simulated arms 18a and 18b, as will be discussed in further detail below. The upper torso bracket 78 includes a back plate 82, side plates 84a and 84b, and a neck plate 86. The neck plate 86 extends upwardly (as viewed in FIG. 12) from the back plate 82, and the side plates 84a and 84b extend transversely from opposing sides of the back plate 82. Moreover, the side plates 84a and 84b include mounting plates 88a and 88b, respectively, extending transversely therefrom, and the neck plate 86 includes a mounting plate 90 extending transversely therefrom. The simulated arms 18a and 18b are operably coupled to the mounting plates 88a and 88b, respectively, via articulation joints 92a and 92b, and the simulated head 12 is operably coupled to the mounting plate 90 via an articulation joint 94. In several exemplary embodiments, the articulation joints 92a, 92b, and 94 are substantially identical to one another, and, therefore, in connection with FIG. 13, only the articulation joint 92a will be described in detail below; however, the description below applies to every one of the articulation joints 92a, 92b, and 94.

Figure 13:
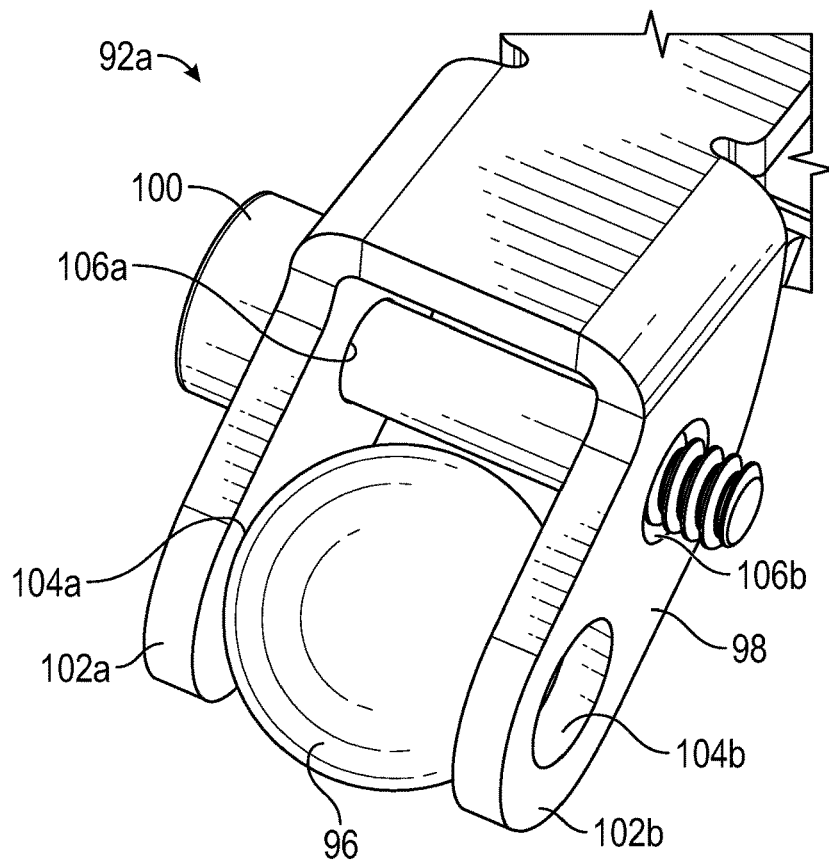
FIG. 13 is a perspective view of the articulation joint(s) of FIG. 11, according to an exemplary embodiment.

Turning to FIG. 13, the articulation joint 92a includes a ball 96, a clamp 98, and a clamp screw 100. The clamp 98 is a generally U-shaped bracket including jaws 102a and 102b having openings 104a and 104b, respectively, formed therethrough. The openings 104a and 104b receive and maintain the ball 96 between the jaws 102a and 102b. The jaws 102a and 102b further include a through-hole 106a and a threaded hole 106b, respectively. The clamp screw 100 extends through the through-hole 106a and threadably engages the threaded hole 106b to adjust the clamping force exerted by the jaws 102a and 102b on the ball 96. As discussed above, the simulated arm 18a is operably coupled to the mounting plate 88a via the articulation joint 92a. More particularly, the ball 96 of the articulation joint 92a is connected to the mounting plate 88a of the upper torso bracket 78, and the clamp 98 of the articulation joint 92a is connected to the simulated arm 18a. As a result, the clamping force exerted by the jaws 102a and 102b on the ball 96 determines the arm 18a's resistance to motion about the articulation joint 92a. Referring back to FIG. 12, a clamp 107 is connected to the back plate 82 of the upper torso bracket 78, opposite the neck plate 86. The clamp 107 is substantially identical to the clamp 98 and forms part of an articulation joint that is substantially identical to the articulation joint 92a, as will be discussed in further detail below.

In several exemplary embodiments, the manner in which simulated arm 18b is operably coupled to the mounting plate 88b via the articulation joint 92b is identical to the manner in which the simulated arm 18a is operably coupled to the mounting plate 88a via the articulation joint 92a, and therefore will not be discussed in further detail. In several exemplary embodiments, the manner in which simulated head 12 is operably coupled to the mounting plate 90 via the articulation joint 94 is identical to the manner in which the simulated arm 18a is operably coupled to the mounting plate 88a via the articulation joint 92a, and therefore will not be discussed in further detail.

Figure 14:
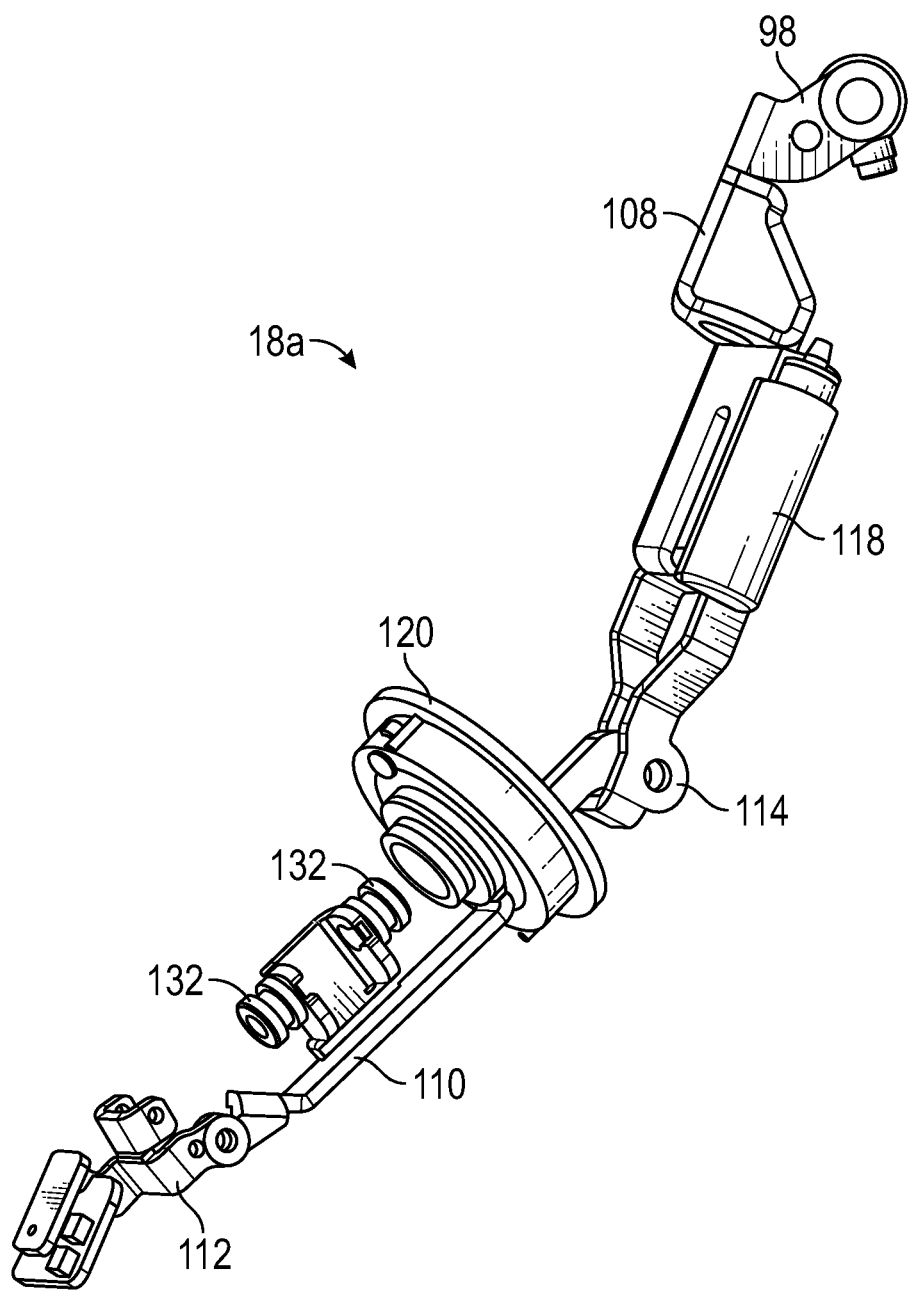
FIG. 14 is a perspective view of the simulated arm(s) of FIGS. 1 and 11 including an upper arm, a forearm, and a hand, the upper arm including a pulse bladder, and the forearm being operably coupled to the upper arm via a spindle, according to an exemplary embodiment.
Figure 15:
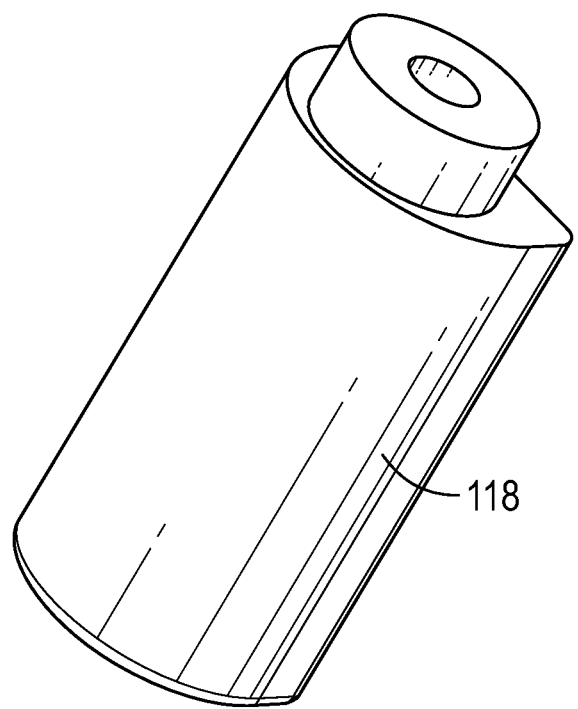
FIG. 15 is a perspective view of the pulse bladder of FIG. 14, according to an exemplary embodiment.
Figure 16:
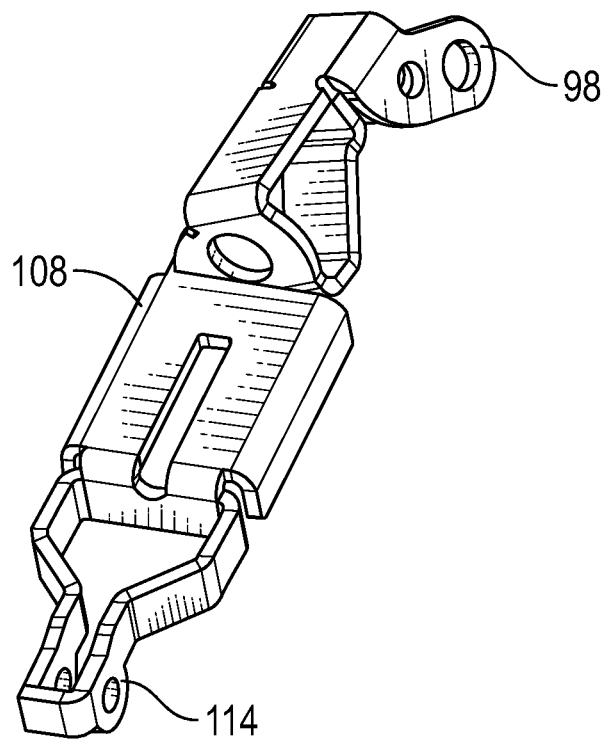
FIG. 16 is a perspective view of the upper arm of FIG. 14, according to an exemplary embodiment.
Figure 17:
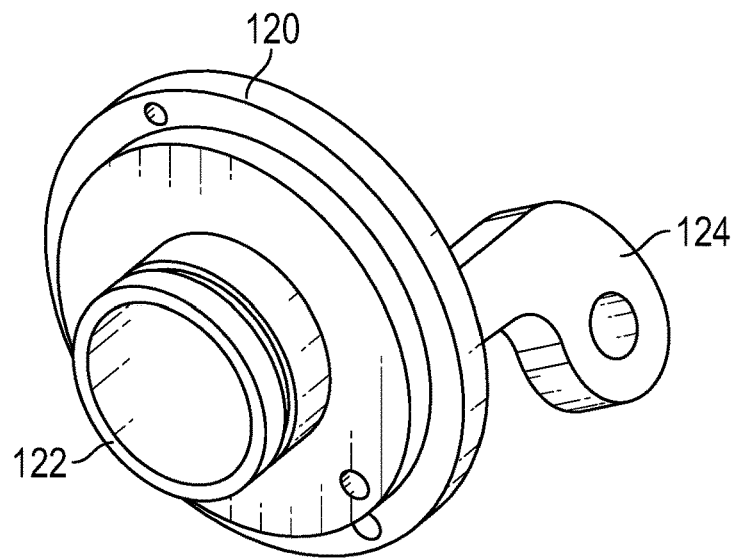
FIG. 17 is a perspective view of the spindle of FIG. 14, according to an exemplary embodiment.
Figure 18:
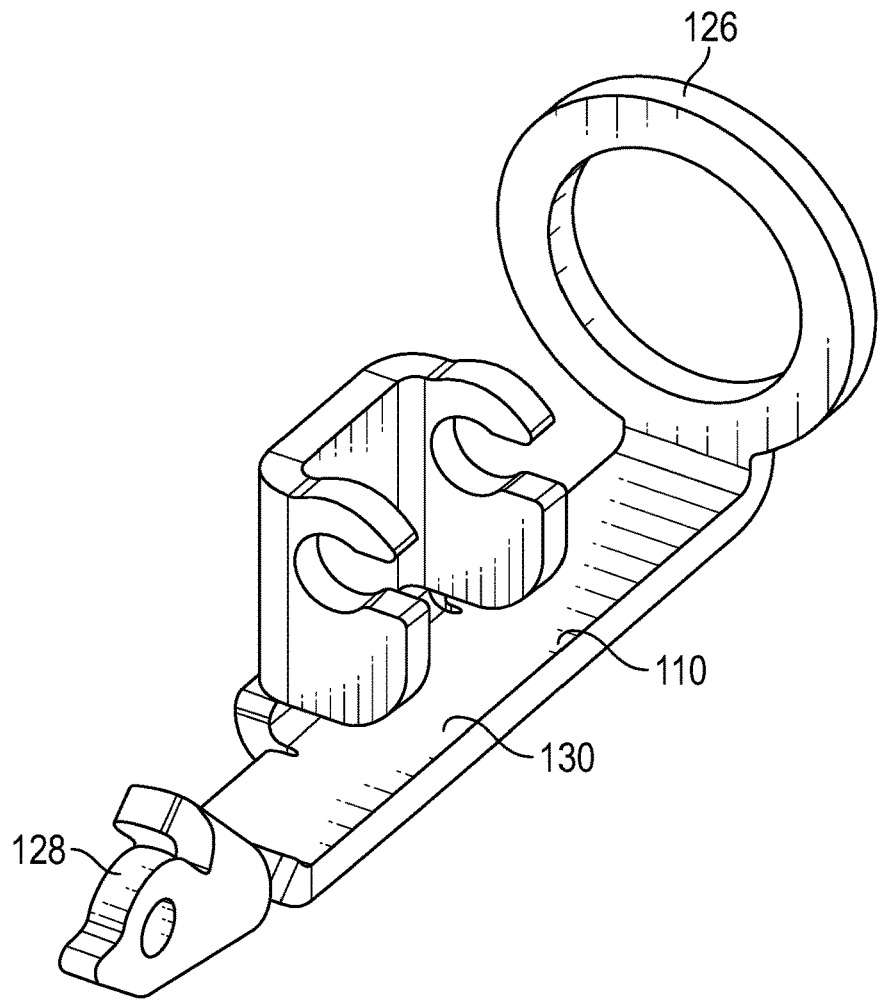
FIG. 18 is a perspective view of the forearm of FIG. 14, according to an exemplary embodiment.
Figure 19:
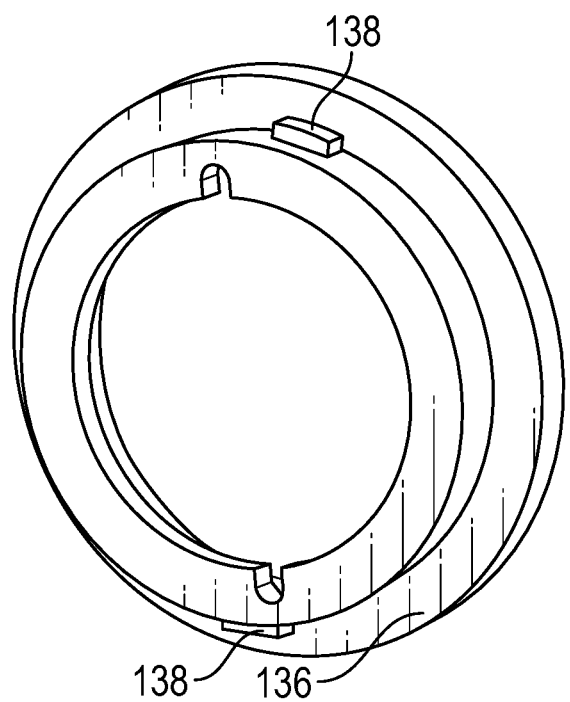
FIG. 19 is a perspective view of a flange that is connected to the spindle of FIGS. 14 and 17, according to an exemplary embodiment.
Figure 20:
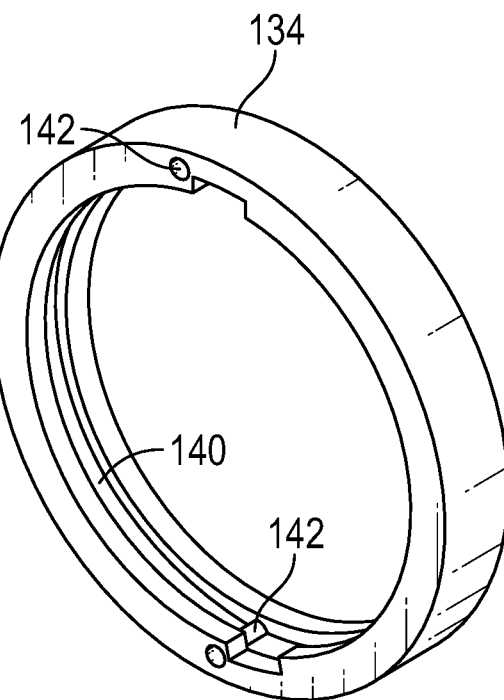
FIG. 20 is a perspective view of a cage connected to an outer skin of the patient simulator system and detachably coupled to the flange of FIG. 19, according to an exemplary embodiment.
Figure 21:
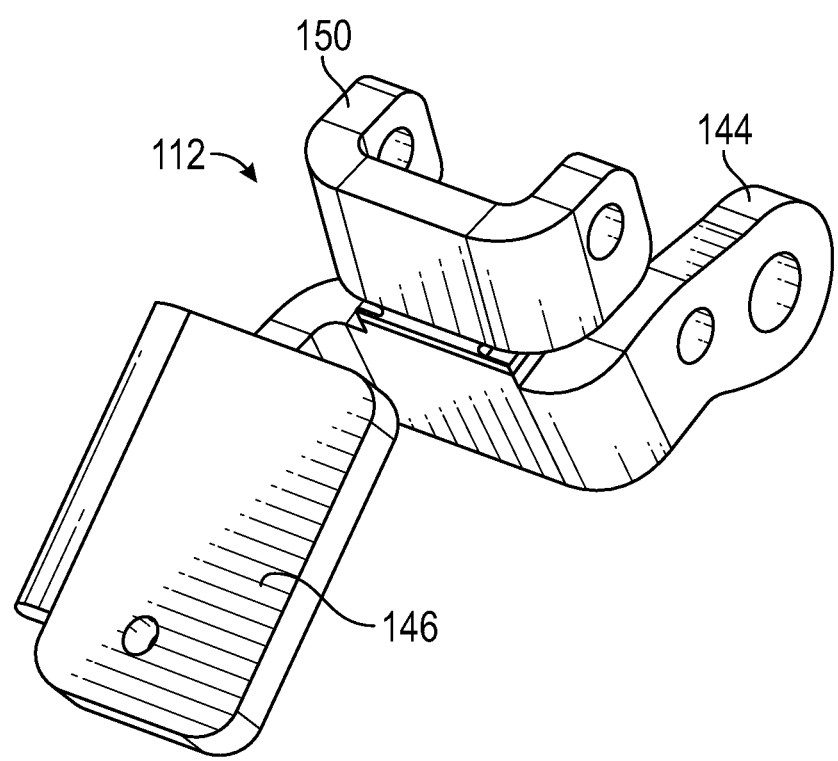
FIG. 21 is a perspective view of the hand of FIG. 14, according to an exemplary embodiment.

In several exemplary embodiments, the simulated arms 18a and 18b are substantially identical to one another, and, therefore, in connection with FIGS. 14-21, only the simulated arm 18a will be described in detail below; however, the description below applies to both of the simulated arms 18a and 18b. Turning to FIG. 14, the simulated arm 18a includes an upper arm 108, a forearm 110, and a hand 112. The clamp 98 of the articulation joint 92a is connected to the upper arm 108. The upper arm 108 includes a pivot bracket 114, opposite the clamp 98. A shoulder insert 116 and a pulse module 118 (to which the simulated circulatory system provides the pneumatic or hydraulic pulse) are operably coupled to the upper arm 108. To simulate the pronation and supination of a forearm and the planar rotation of an elbow joint, the forearm 110 is operably coupled to the upper arm 108 via a spindle 120. The spindle 120 includes a hub 122 and a pivot bracket 124. The pivot bracket 124 of the spindle 120 is pivotably coupled to the pivot bracket 114 of the upper arm 108. The forearm 110 includes a swivel ring 126, a pivot bracket 128 opposite the swivel ring 126, and a mounting plate 130 to which one or more guide tube fittings 132 are operably coupled. The swivel ring is 126 rotatably and detachably coupled to the hub 122 of the spindle 120. Additionally, a cage 134 is attached to the simulated skin (not shown) of the forearm 110, and a flange 136 is connected to the spindle 120. The flange 136 includes tabs 138. The cage 134 includes an internal raceway 140 to accommodate the tabs 138 of the flange 136, and coil pins 142 to lock the tabs 138 into position within the internal raceway 140. In this manner, the cage 134 is rotatably and detachably coupled to the flange 136 so that the forearm 110 and the simulated skin of the forearm 110 are each permitted to rotate relative to, and detach from, the spindle 120. The hand 112 includes a pivot bracket 144 pivotably coupled to the pivot bracket 128 of the forearm 110, a mounting plate 146 to which an electronic circuit board 148 is connected, and an actuation plate 150 to which an arm actuation line (not shown) of the simulated arm 18a is connected.

Referring back to FIG. 11, the arm motor 80a is connected to the side plate 84a of the upper torso bracket 78 to actuate the arm actuation line, which arm actuation line is routed through tubing (not shown) from the arm motor 80a, through the hub 122 of the spindle 120 and guide tube fittings 132 of the forearm 110, and to the actuation plate 150 of the hand 112. The retrieval of the arm actuation line by the arm motor 80a produces a first moment between the forearm 110 and the hand 112 at the pivotable connection between the respective pivot brackets 128 and 144 thereof. The first moment causes the hand 112 to pivot about the pivotable connection between the pivot brackets 128 and 144, and relative to the forearm 110. The retrieval of the arm actuation line by the arm motor 80*a* also produces a second moment between the upper arm 108 and the forearm 110 at the pivotable connection between the respective pivot brackets 114 and 128 thereof. The second moment causes the forearm 110 to pivot about the pivotable connection between the pivot brackets 114 and 128, and relative to the upper arm 108. In several exemplary embodiments, during the retrieval of the arm actuation line by the arm motor 80*a*, the first moment pivots the hand 112 relative to the forearm 110 before the second moment pivots the forearm 110 relative to the upper arm 108. The subsequent payout of the arm actuation line by the arm motor 80*a* permits relaxation of the simulated arm 18*a* according to gravity and the elastic properties of the simulated skin 22.

Figure 22:
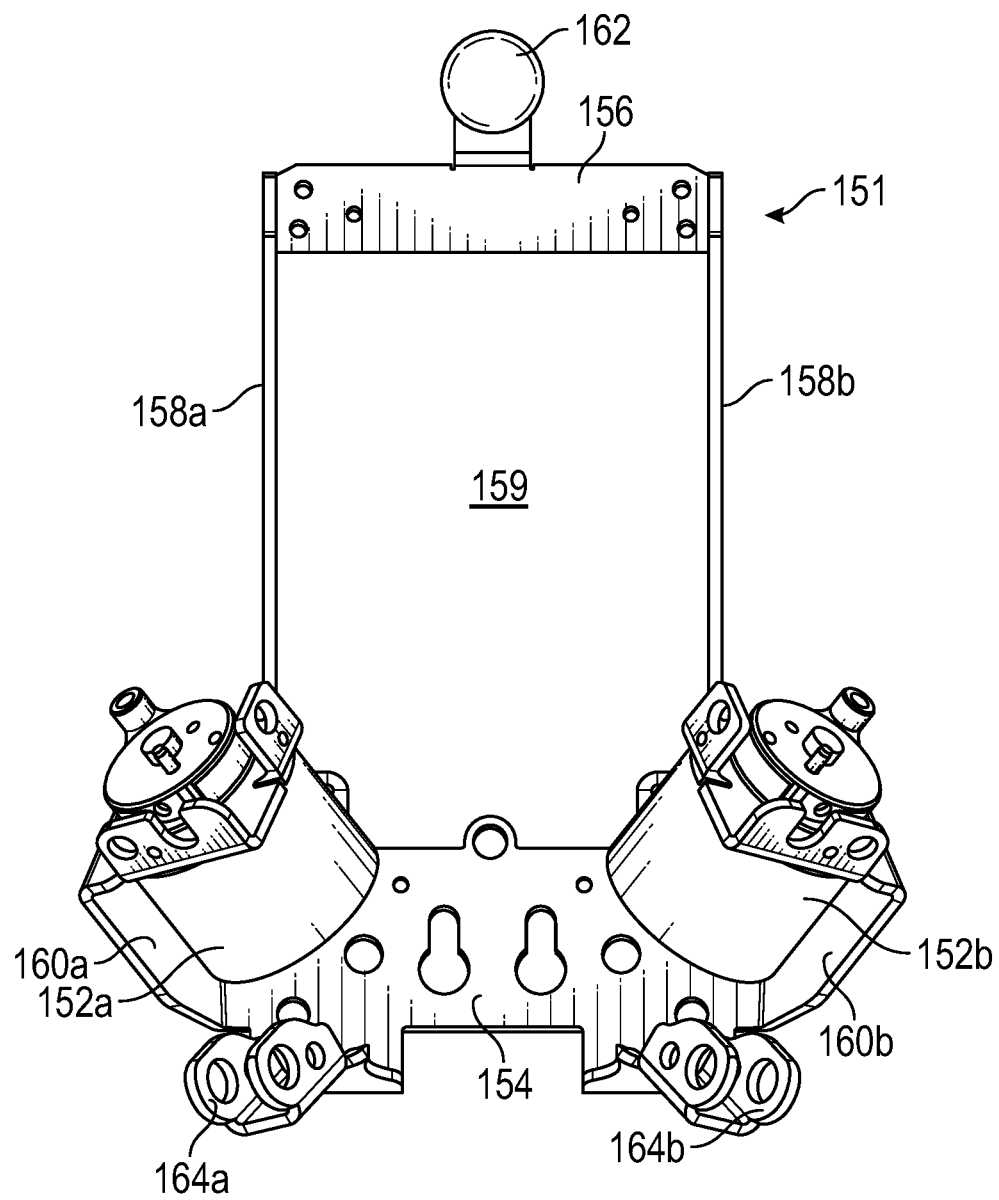
FIG. 22 is an elevational view of a lower torso bracket operably coupled to the upper torso bracket of FIGS. 11 and 12 and the simulated legs of FIG. 1, according to an exemplary embodiment.
Figure 23:
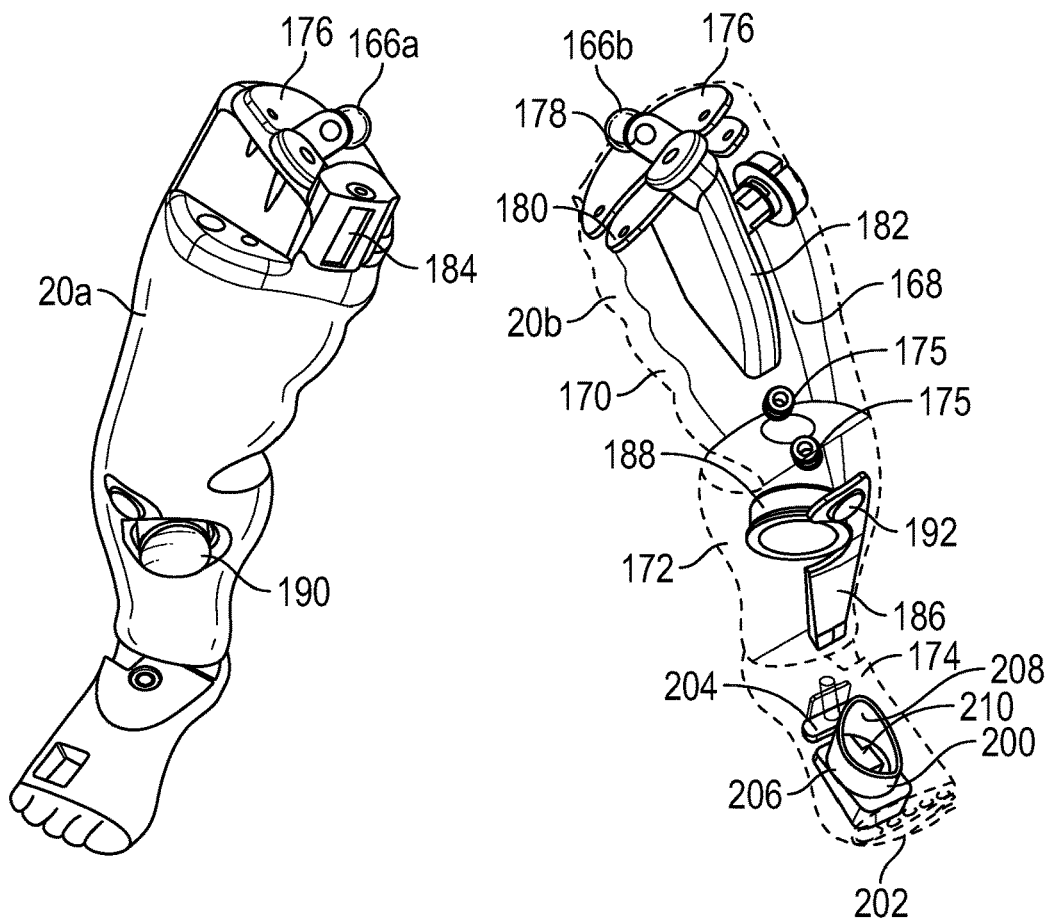
FIG. 23 is a perspective view of the simulated legs of FIG. 1, the simulated legs each including an intraosseous (IO) assembly, according to an exemplary embodiment.

In an exemplary embodiment, as illustrated in FIGS. 22 and 23, the simulated legs 20*a* and 20*b* are operably coupled to a lower torso bracket 151. Also connected to the lower torso bracket 151 are a pair of leg motors 152*a* and 152*b* for actuating the simulated legs 20*a* and 20*b*, respectively, as will be discussed in further detail below. The lower torso bracket 151 includes a back plate 154, a top plate 156, support plates 158*a* and 158*b*, and side plates 160*a* and 160*b*. The side plates 160*a* and 160*b* support the leg motors 152*a* and 152*b*, respectively, and extend transversely from opposing sides of the back plate 154. The support plates 158*a* and 158*b* extend upwardly from the back plate 154, and the top plate 156 is connected to the support plates 158*a* and 158*b*. As a result, an empty space 159 is defined between the back plate 154, the top plate 156, and the support plates 158*a* and 158*b*.

A ball 162 is connected to the top plate 156. The ball 162 is substantially identical to the ball 96 and forms part of an articulation joint that is substantially identical to the articulation joint 92*a*. The articulation joint of which the ball 162 is a part also includes the clamp 107 connected to the back plate 154 of the upper torso bracket 78. As a result, the upper torso bracket 78 is operably coupled to the lower torso bracket 151 via the articulation joint (including the ball 162 and the clamp 107) in a manner substantially identical to the manner in which the simulated arm 18*a* is operably coupled to the mounting plate 88*a* via the articulation joint 92*a*.

Clamps 164*a* and 164*b* are connected to the back plate 154, adjacent the side plates 160*a* and 160*b*. The clamps 164*a* and 164*b* are substantially identical to the clamp 98 and each form part of an articulation joint that is substantially identical to the articulation joint 92*a*. The articulation joints of which the clamps 164*a* and 164*b* are a part also include balls 166*a* and 166*b* connected to the simulated legs 20*a* and 20*b*, respectively. As a result, the lower torso bracket 151 is operably coupled to the simulated legs 20*a* and 20*b* via the respective articulation joints (including the clamps 164*a* and 164*b* and the balls 166*a* and 166*b*) in a manner similar to the manner in which the simulated arm 18*a* is operably coupled to the mounting plate 88*a* via the articulation joint 92*a*.

In several exemplary embodiments, the simulated legs 20*a* and 20*b* are substantially identical to one another, and, therefore, in connection with FIG. 23, only the simulated leg 20*b* will be described in detail below; however, the description below applies to both of the simulated legs 20*a* and 20*b*. Turning to FIG. 23, the simulated leg 20*b* includes a leg insert 168 defining an upper leg 170, a lower leg 172, and a foot 174, each providing mounting structure for various other components of the simulated leg 20*b*. The size and shape of the leg insert 168 are configured to simulate a patient's leg movement when the simulated leg 20*b* is actuated. The actuation of the simulated leg 20*b* is facilitated by one or more guide tube fittings 175 embedded in the upper leg 170 and the lower leg 172, as will be discussed in further detail below.

The upper leg 170 engages an external support plate 176 that includes a mounting plate 178 extending transversely therefrom. The ball 166*b* of the simulated joint (connecting the simulated leg 20*b* to the lower torso bracket 151) is connected to the mounting plate 178. Embedded in the upper leg 170 is a sandwich plate 180 that is connected to the support plate 176 so that a portion of the upper leg 170 is sandwiched between the support plate 176 and the sandwich plate 180. As a result, the sandwich plate 180, the support plate 176, and the ball 166*b* together support the upper leg 170 and facilitate articulation of the leg insert 168 about the simulated joint connecting the simulated leg 20*b* to the lower torso bracket 151. A leg expansion bag 182 and a pulse module 184 (to which the simulated circulatory system provides the pneumatic or hydraulic pulse) are embedded in the upper leg 170.

Figure 24:
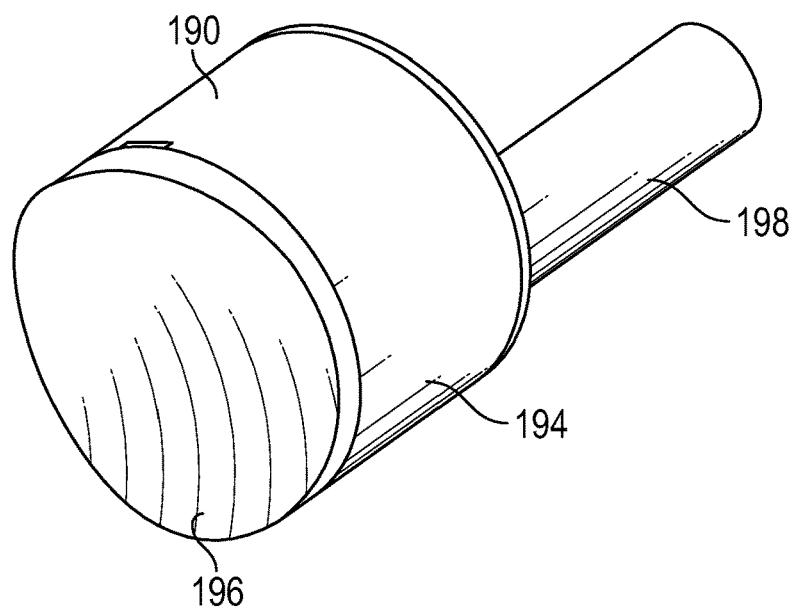
FIG. 24 is a perspective view of the IO assembly of FIG. 23, according to an exemplary embodiment.

The lower leg 172 is pivotably coupled to the upper leg 170. Operably coupled to the lower leg 172 are a simulated intraosseous (IO) bone 186, an IO retaining clip 188, and an IO assembly 190. The simulated IO bone 186 simulates a patient's tibia and provides structural reinforcement of the leg insert 168 during actuation of the simulated leg 20*b*. The simulated IO bone 186 includes a protrusion 192 that simulates an anatomical landmark known as the tibial tuberosity. The IO retaining clip 188 is embedded in the lower leg 172 and receives the IO assembly 190 adjacent the simulated IO bone 186. Turning to FIG. 24, the IO assembly 190 includes a reservoir 194 and a skin pad 196 that inlays with the skin 22 of the lower leg 172. A drainage tube 198 is connected to the reservoir 194 of the IO assembly 190 and routed through the back of the lower leg 172. In several exemplary embodiments, the simulated IO bone 186 and the IO assembly 190 may be used to perform an IO infusion training procedure.

Referring back to FIG. 23, the foot 174 is pivotably coupled to the lower leg 172. Operably coupled to the foot 174 are a capillary press to refill (CPTR) assembly 200, a foot cyanosis insert 202, and a leg actuation line tie-off 204. The CPTR assembly 200 includes a CPTR housing 206 and a CPTR lens 208. The CPTR housing 206 is embedded in the foot 174 and houses the CPTR housing 206 along with a pressure sensor (not shown), an LED (not shown), and a CPTR circuit board (not shown). The CPTR lens 208 is a semi-transparent component that disperses light from the LED in the form of a thumb print, and includes a recess 210 for the CPTR circuit board on its lower surface. The combination of the CPTR lens 208, the pressure sensor, the LED and the CPTR circuit board together simulate the effect of pressing a patient's skin to force blood out of the pressed area, and releasing the patient's skin to allow the return of blood to the pressed area. The CPTR assembly 200 further includes an integrated lever (not shown) used to depress the pressure sensor and activate the CPTR assembly 200. The foot cyanosis insert 202 is a transparent (or semi-transparent) component embedded at the tip of the foot 174 that disperses blue light to simulate a cyanotic state. The leg actuation line tie-off 204 is embedded in the foot 174 and provides an anchor point for a leg actuation line (not shown) of the simulated leg 20*b*.

Referring back to FIG. 22, the leg motor 152b is connected to the side plate 160b of the lower torso bracket 151 to actuate the leg actuation line, which leg actuation line is routed through tubing (not shown) from the leg motor 152b, through the guide tube fittings 175 of the leg insert 168, and to the leg actuation line tie-off 204 of the foot 174. The retrieval of the leg actuation line by the leg motor 152b produces a third moment between the lower leg 172 and the foot 174 at the pivotable connection therebetween. The third moment causes the foot 174 to pivot about said pivotable connection and relative to the lower leg 172. The retrieval of the leg actuation line by the leg motor 152b also produces a fourth moment between the upper leg 170 and the lower leg 172 at the pivotable connection therebetween. The fourth moment causes the lower leg 172 to pivot about said pivotable connection and relative to the upper leg 170. In several exemplary embodiments, during the retrieval of the leg actuation line by the leg motor 152b, the third moment pivots the foot 174 relative to the lower leg 172 before the fourth moment pivots lower leg 172 relative to the upper leg 170. The subsequent payout of the leg actuation line by the leg motor 152b permits relaxation of the simulated leg 20b according to gravity and the elastic properties of the leg insert 168 and the simulated skin 22.

Figure 25:
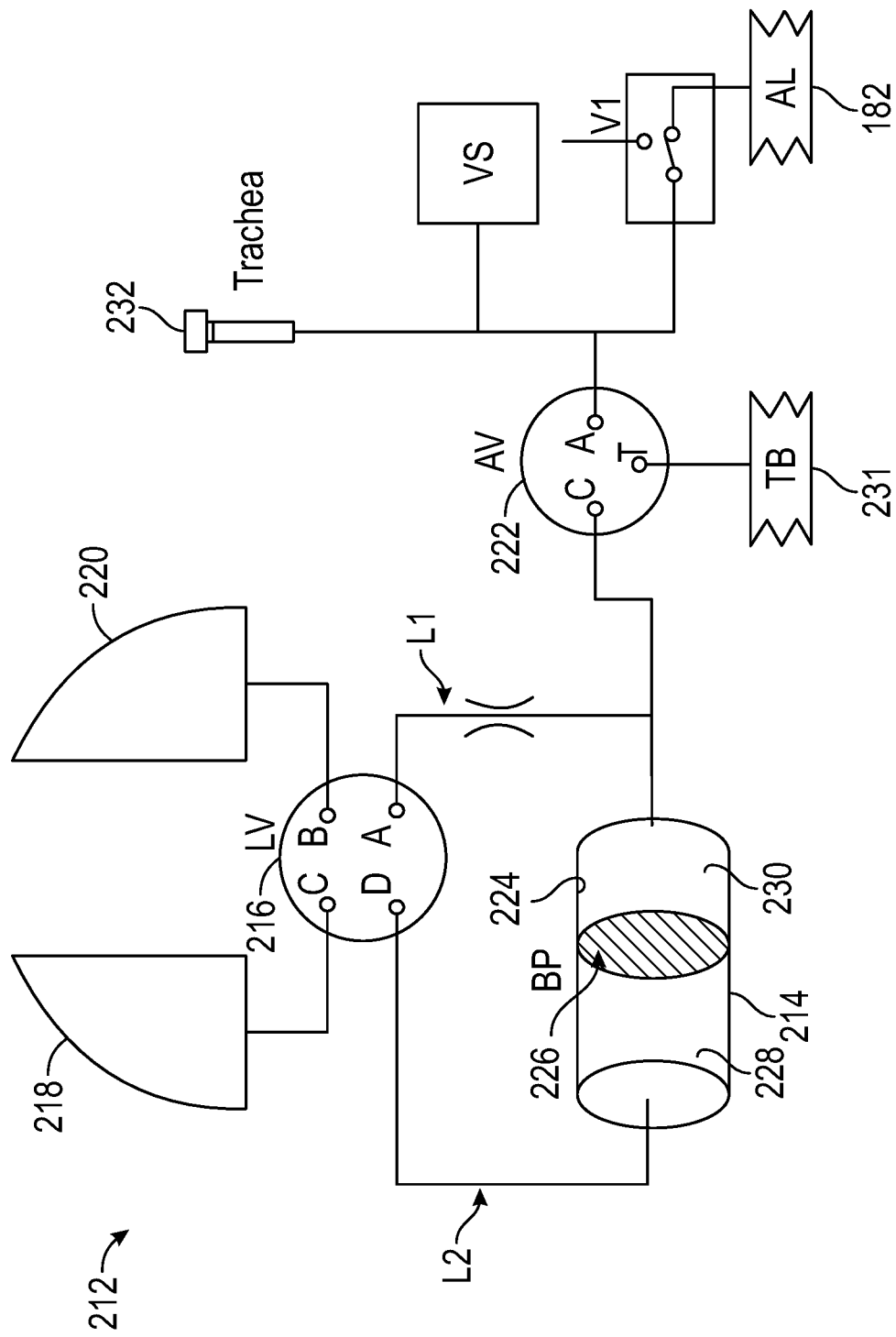
FIG. 25 is a diagrammatic view of a simulated respiratory system adapted to be operably coupled to patient simulator system of FIG. 1, the simulated respirator system including simulated lungs, a lung valve, a breathing pump, an airway valve, an abdominal expansion bag, a leg expansion bag, and an airway system, according to an exemplary embodiment.
Figure 26:
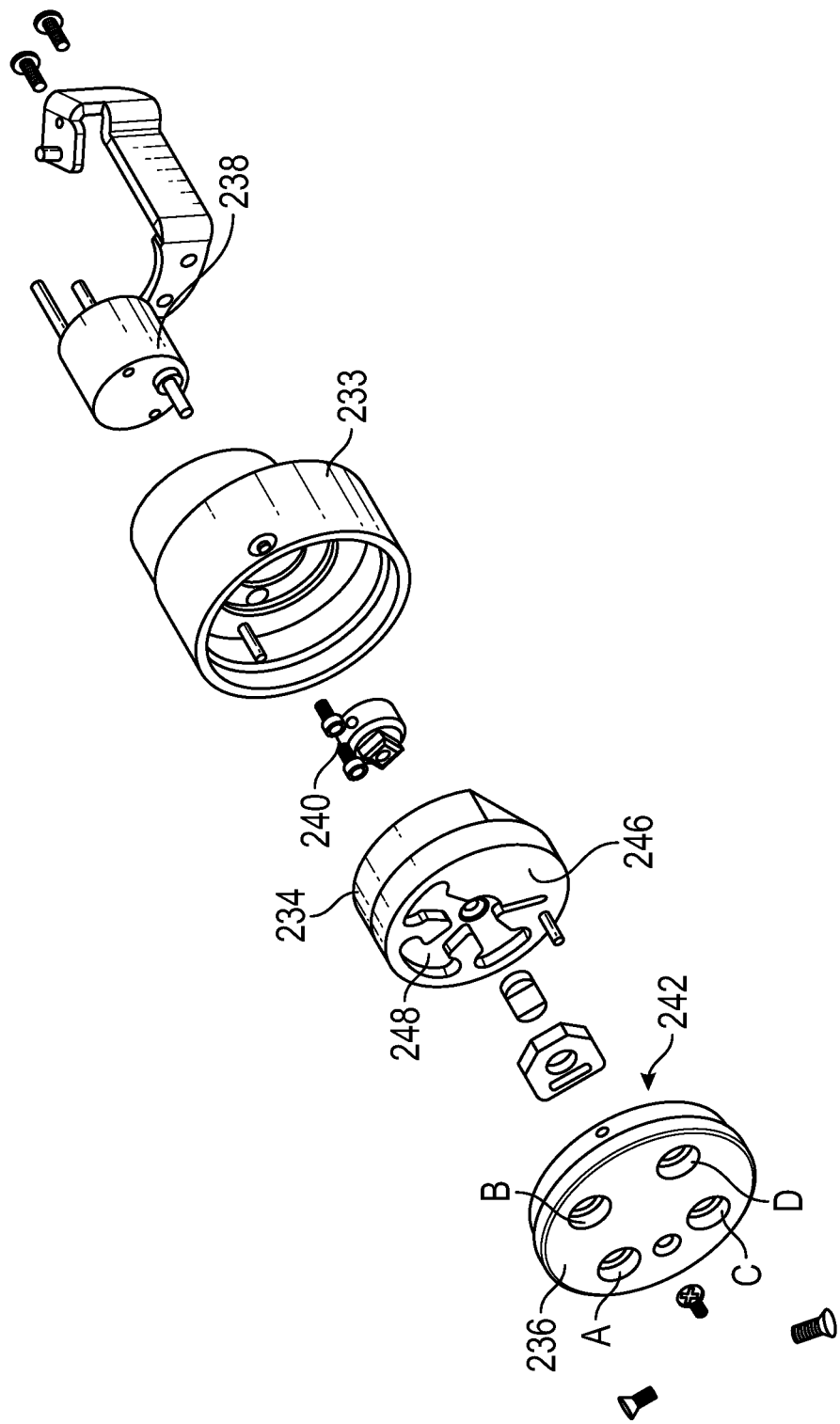
FIG. 26 is an exploded view of the lung valve of FIG. 25 including a distributor and a valve lid, according to an exemplary embodiment.
Figure 27:
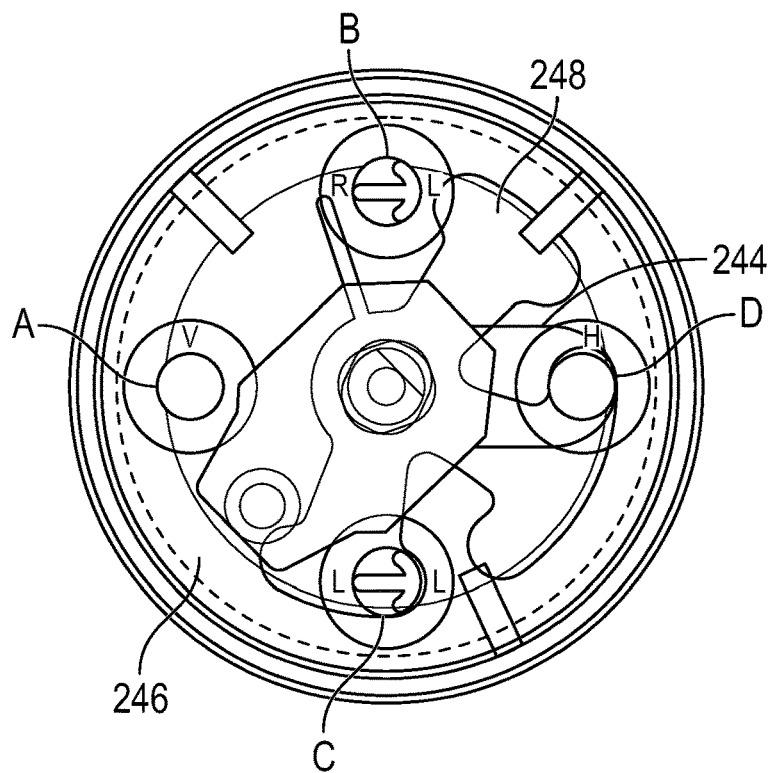
FIG. 27 is an elevational view of the lung valve of FIGS. 25 and 26 with the distributor in a first rotational position, according to an exemplary embodiment.
Figure 28:
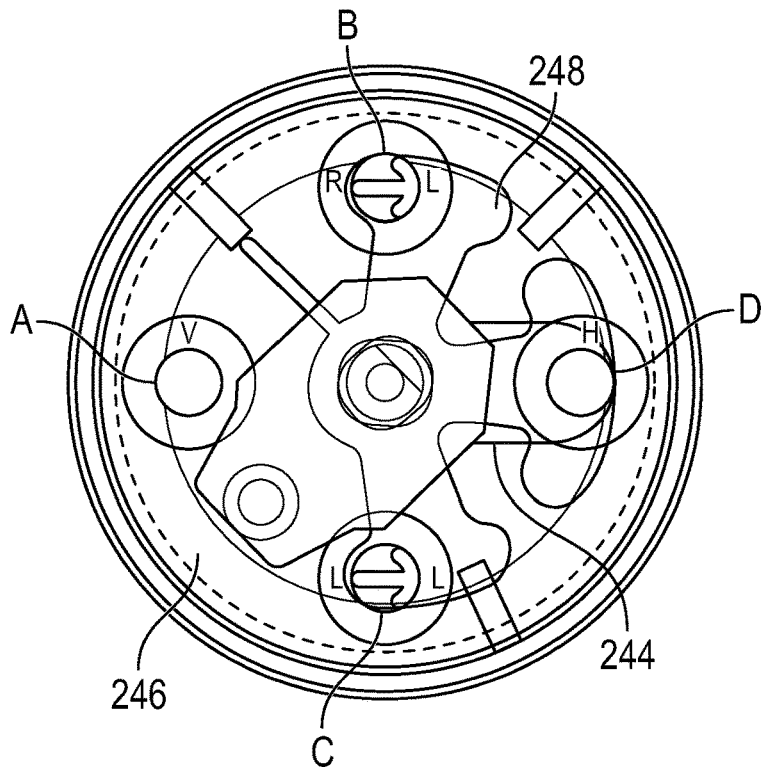
FIG. 28 is an elevational view of the lung valve of FIGS. 25-27 with the distributor in a second rotational position, according to an exemplary embodiment.
Figure 29:
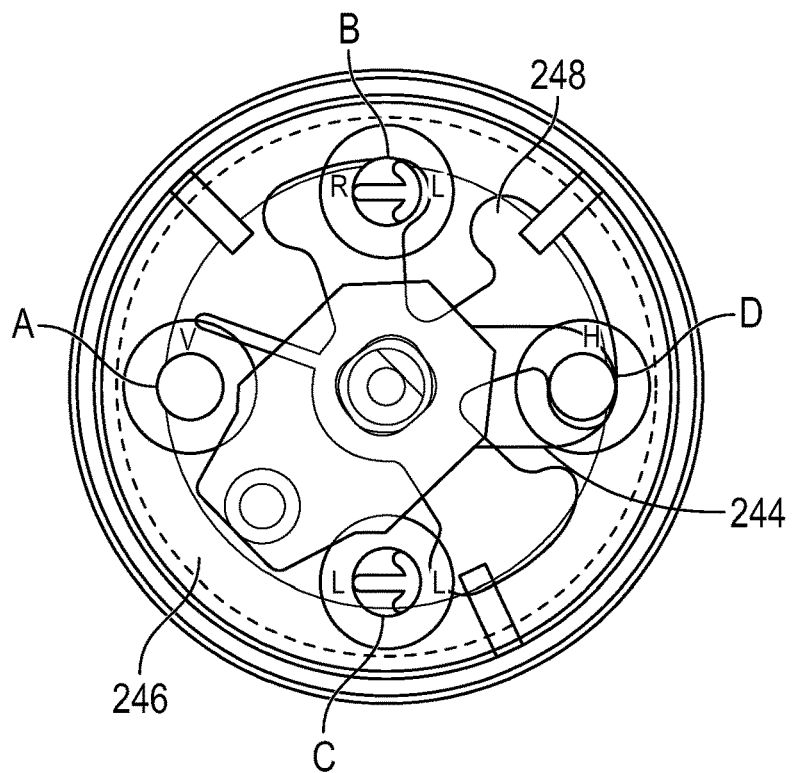
FIG. 29 is an elevational view of the lung valve of FIGS. 25-28 with the distributor in a third rotational position, according to an exemplary embodiment.
Figure 30:
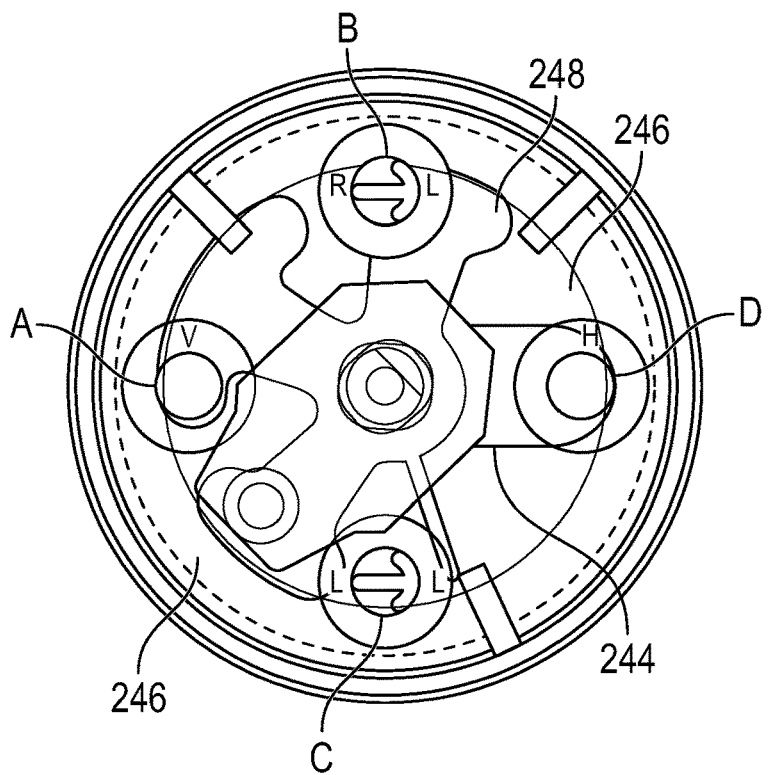
FIG. 30 is an elevational view of the lung valve of FIGS. 25-29 with the distributor in a fourth rotational position, according to an exemplary embodiment.
Figure 31:
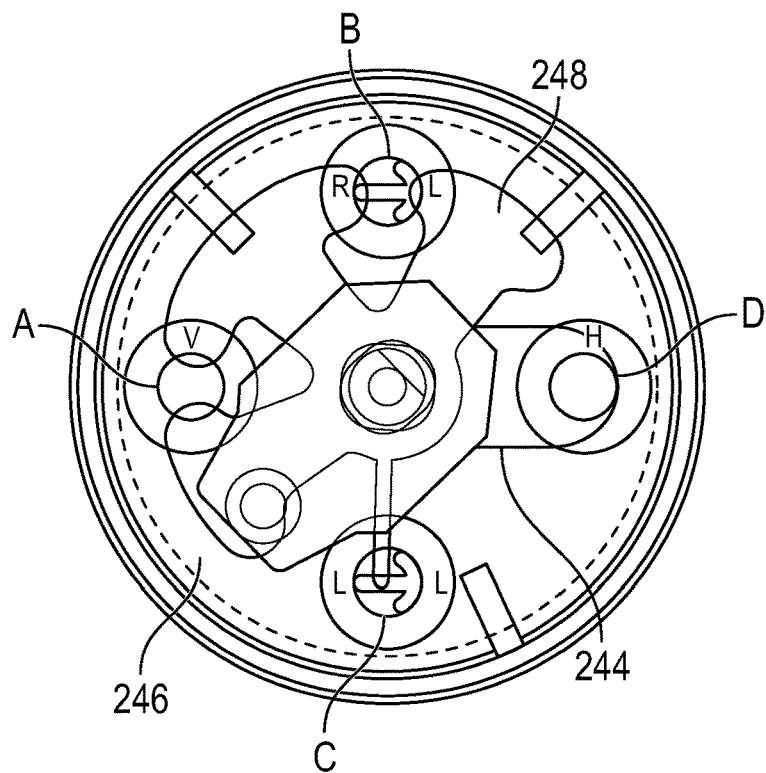
FIG. 31 is an elevational view of the lung valve of FIGS. 25-30 with the distributor in a fifth rotational position, according to an exemplary embodiment.
Figure 32:
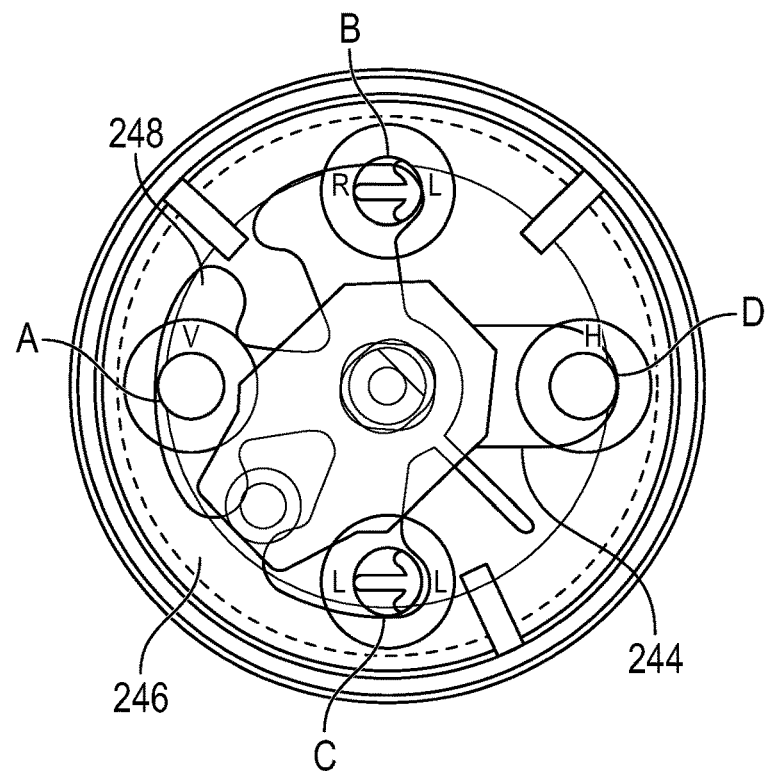
FIG. 32 is an elevational view of the lung valve of FIGS. 25-31 with the distributor in a sixth rotational position, according to an exemplary embodiment.
Figure 33:
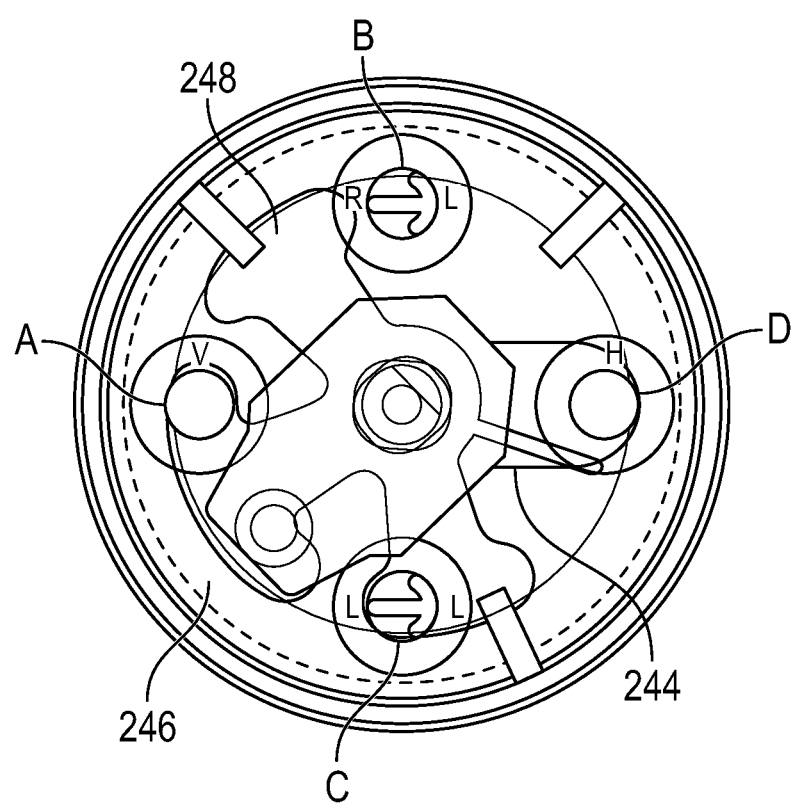
FIG. 33 is an elevational view of the lung valve of FIGS. 25-32 with the distributor in a seventh rotational position, according to an exemplary embodiment.

In an exemplary embodiment, as illustrated in FIG. 25, the patient simulator system 10 includes a simulated respiratory system 212 including a breathing pump 214, a lung valve 216, simulated left and right lungs 218 and 220, and an airway valve 222. The breathing pump 214 includes a cylinder 224 and a piston 226 dividing the cylinder 224 into chambers 228 and 230. During the upward stroke of the piston 226 (from right to left as viewed in FIG. 25), the breathing pump 214 generates positive pressure in the chamber 228 and negative (vacuum) pressure in the chamber 230. Conversely, during the downward stroke of the piston 226 (from left to right as viewed in FIG. 25), the breathing pump 214 generates negative (vacuum) pressure in the chamber 228 and positive pressure in the chamber 230.

The lung valve 216 includes breathing ports A, B, C, and D. The breathing port A of the lung valve 216 communicates, via a line L1, with both the airway valve 222 and the chamber 230 of the breathing pump 214. The breathing port B of the lung valve 216 communicates with the simulated right lung 220. The breathing port C of the lung valve 216 communicates with the simulated left lung 218. The breathing port D of the lung valve 216 communicates with the chamber 228 of the breathing pump 214 via a line L2, which is larger in diameter than the line L1. Further, the airway valve 222 includes airway ports C, T, and A. The airway port C of the airway valve 222 communicates, via the line L1, with both the chamber 230 of the breathing pump 214 and the breathing port A of the lung valve 216. The airway port T of the airway valve 222 communicates with an abdominal expansion bag 231. The airway port A of the airway valve 222 communicates with both an airway system 232 and the leg expansion bag(s) 182 of the simulated legs 20a and 20b.

The lung valve 216 is configurable between a spontaneous breathing configuration in which the breathing port D is in communication with one or both of the breathing ports B and C, and an assisted breathing configuration in which both of the breathing ports A and D are in communication with one or both of the breathing ports B and C. Similarly, the airway valve 222 is configurable between an airway configuration in which the airway port A is in communication with the airway port C, and an abdominal configuration in which the airway port C is in communication with the airway port T. Accordingly, the simulated respiratory system 212 is operated by precisely controlling the respective configurations of the lung valve 216 and the airway valve 222, along with the breathing amplitude and frequency generated by the piston 226.

In operation, when the lung valve 216 is in the spontaneous breathing configuration and the airway valve 222 is in the airway configuration: each upward stroke of the piston 226 forces air from the chamber 228 into one or both of the simulated left and right lungs 218 and 220 via the line L1 and produces a negative (vacuum) pressure in the airway system 232; and each downward stroke of the piston 226 draws air out of one or both of the simulated left and right lungs 218 and 220 into the chamber 228 via the line L1 and produces a positive pressure in the airway system 232. As a result, the upward and downward strokes of the piston 226 (when the lung valve 216 is in the spontaneous breathing configuration and the airway valve 222 is in the airway configuration): simulate the rise and fall of a patient's chest cavity; and cause the airway system 232 to inhale and exhale in a manner that simulates a patient's breathing pattern.

Further, when the lung valve 216 is in the spontaneous breathing configuration and the airway valve 222 is in the abdominal configuration: each upward stroke of the piston 226 produces a negative (vacuum) pressure in the abdominal expansion bag 231 and forces air from the chamber 228 into one or both of the simulated left and right lungs 218 and 220 via the line L1; and each downward stroke of the piston 226 produces a positive pressure in the abdominal expansion bag 231 and draws air out of one or both of the simulated left and right lungs 218 and 220 into the chamber 228 via the line L1. As a result, the upward and downward strokes of the piston 226 (when the lung valve 216 is in the spontaneous breathing configuration and the airway valve 222 is in the abdominal configuration): simulate the rise and fall of a patient's chest cavity; and cause the abdominal expansion bag 231 to deflate and inflate, respectively, in a manner that simulates respiratory distress in a patient (i.e., tummy retractions).

Finally, when the lung valve 216 is in the assisted breathing configuration and the airway valve 222 is in the airway configuration: each upward stroke of the piston 226 produces a negative (vacuum) pressure in the airway system 232 while permitting the escape of air from the lung valve 216 to the airway system 232 via the line L1; and each downward stroke of the piston 226 produces a positive pressure in the airway system 232 while permitting the escape of air from the airway system 232 to the lung valve 216 via the line L1. As a result, the upward and downward strokes of the piston 226 (when the lung valve 216 is in the assisted breathing configuration and the airway valve 222 is in the airway configuration) produce a pressure fluctuation in the airway system 232 that simulates a patient gasping for breath. This pressure fluctuation is sensed by a ventilator (not shown) operably coupled to the airway system 232, which ventilator is then activated to assist (i.e., ventilate) the simulated respiratory system 212. Once the ventilator has been activated, it communicates with both the airway valve 222 and the leg expansion bag(s) 182 (via, for example, a valve V1). Thus, the leg expansion bag(s) 182 accommodate any excess air forced into the simulated respiratory system 212 by the activated ventilator. Alternatively, the valve V1 may be used to prevent, or at least reduce, communication between the ventilator and the leg expansion bag(s) 182, thereby simulating a patient with reduced lung compliance.

In an exemplary embodiment, as illustrated in FIGS. 26-33, the lung valve 216 includes a valve body 233, a distributor 234, and a valve lid 236. The valve body 233 houses the distributor 234. A valve motor 238 is operably coupled to the distributor 234 via a motor coupling 240. The breathing ports A, B, C, and D are formed through the valve lid 236. In an exemplary embodiment, the breathing ports A, B, C, and D are spaced apart along a circumference of the valve lid 236 at about 90-degree intervals. In several exemplary embodiments, the breathing ports A, B, C, and D are spaced apart along a circumference of the valve lid 236 at intervals ranging from about 80-degrees to about 100-degrees. The valve lid 236 includes an end face 242 defining a fluid relief 244 that extends from the breathing port D. The distributor 234 includes an end face 246 defining a fluid relief 248. The valve lid 236 is connected to the valve body 233 to encase the distributor 234 so that the end face 242 of the valve lid 236 sealingly engages the end face 246 of the distributor 234. The circumferential position of the distributor 234 relative to the valve lid 236 is determined using an encoder shaft operably coupled to the distributor 234 and a potentiometer operably coupled to the valve lid 236. The fluid relief 244 in the end face 242 of the valve lid 236 is shaped so that, regardless of the circumferential orientation of the distributor 234, the breathing port D is in fluid communication with the fluid relief 248 on the end face 246 of the distributor 234. Moreover, the fluid relief 248 on the end face 246 of the distributor 234 is shaped so that the lung valve 216 is actuable, via rotation of the distributor 234, between the spontaneous breathing configuration and the assisted breathing configuration.

In the spontaneous breathing configuration, the distributor 234 is positionable between: a left lung disabled position (FIG. 28) in which the breathing port D is in communication with the breathing port B but not the breathing port C; a normal breathing position (FIG. 29) in which the breathing port D is in communication with both of the breathing ports B and C; and a right lung disabled position (FIG. 30) in which the breathing port D is in communication with the breathing port C but not the breathing port B. Similarly, in the assisted breathing configuration, the distributor 234 is positionable between: a left lung disabled position (FIG. 31) in which both of the breathing ports A and D are in communication with the breathing port B but not the breathing port C; a restricted flow position (FIG. 32) in which both of the breathing ports A and D are in communication with the breathing ports B and C at a restricted flow rate; a normal breathing position (FIG. 33) in which both of the breathing ports A and D are in communication with the breathing ports B and C at a normal flow rate; and a right lung disabled position (FIG. 34) in which both of the breathing ports A and D are in communication with the breathing port C but not the breathing port B.

Figure 34:
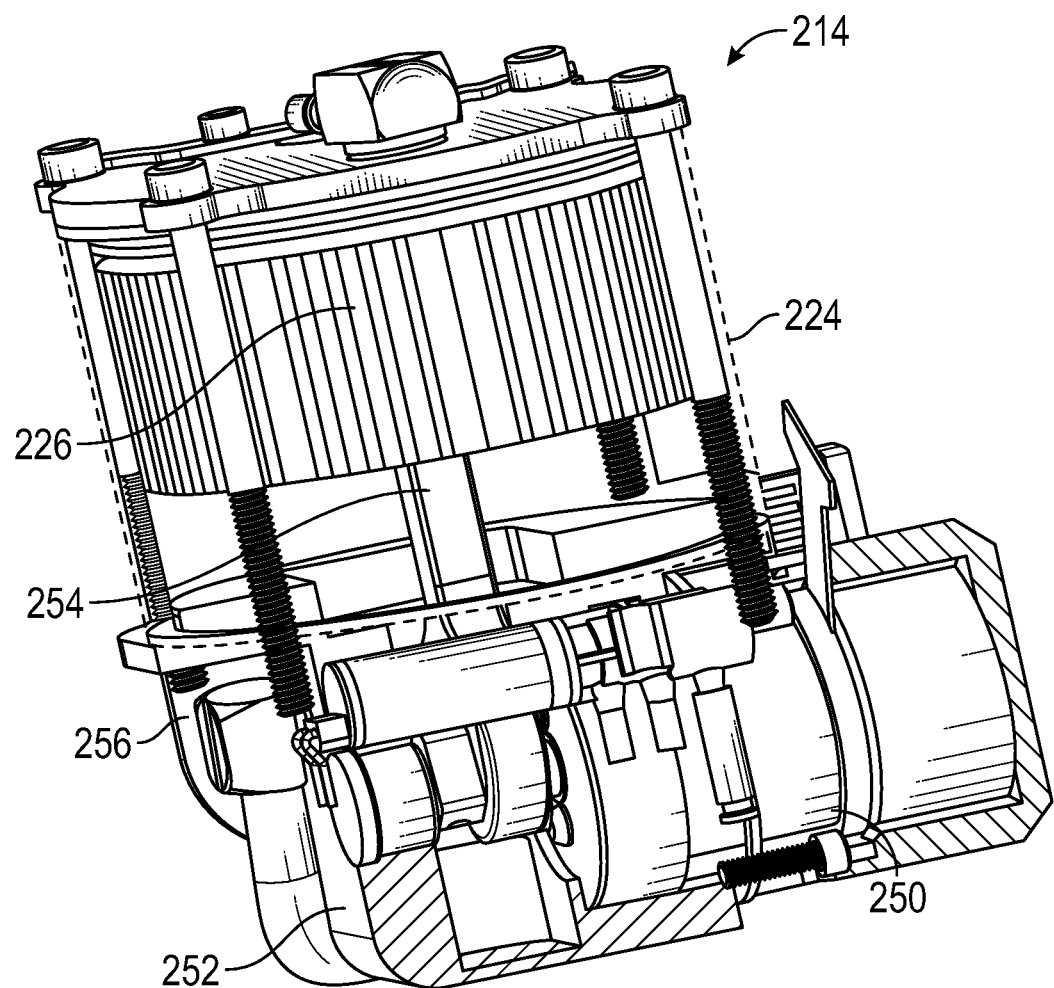
FIG. 34 is a perspective view of the breathing pump of FIG. 25, according to an exemplary embodiment.

In an exemplary embodiment, as illustrated in FIG. 34, the breathing pump 214 includes a motor 250, an eccentric crank (not shown) housed within a crank case 252, a rod 254, the cylinder 224, and the piston 226. The breathing pump 214 may include features to increase efficiency and to prevent, or at least reduce, noise generation. For example, in several exemplary embodiments, the motor 250 is a brushless motor. Further, in several exemplary embodiments, the piston 226 is made of a light self-lubricating material such as, for example, graphite. Further still, in several exemplary embodiments, the cylinder 224 is made of precision-machined glass. The breathing pump 214 further includes a control board 256 operably coupled to the motor 250 to precisely control the breathing amplitude and frequency generated by the piston 226 (via the eccentric crank and the rod 254).

Figure 35:
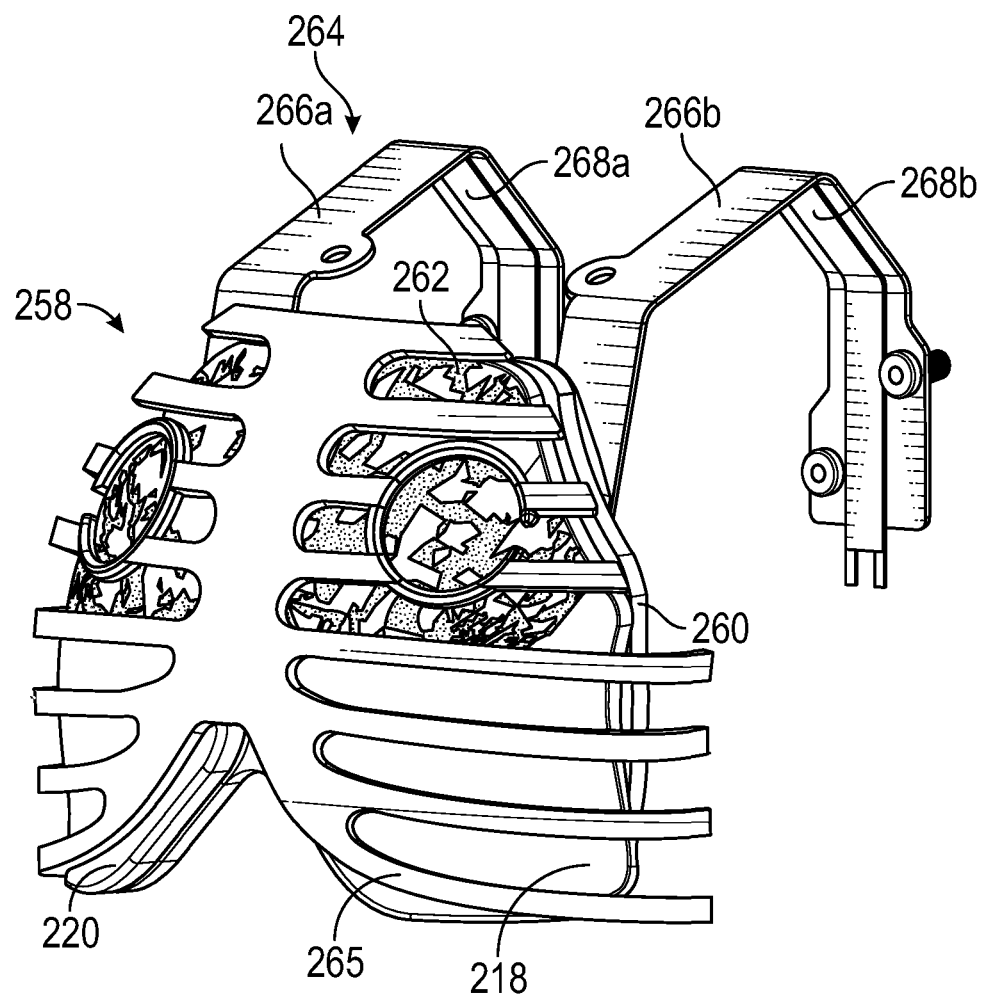
FIG. 35 is a front perspective view of the simulated lungs of FIG. 25, according to an exemplary embodiment.
Figure 36:
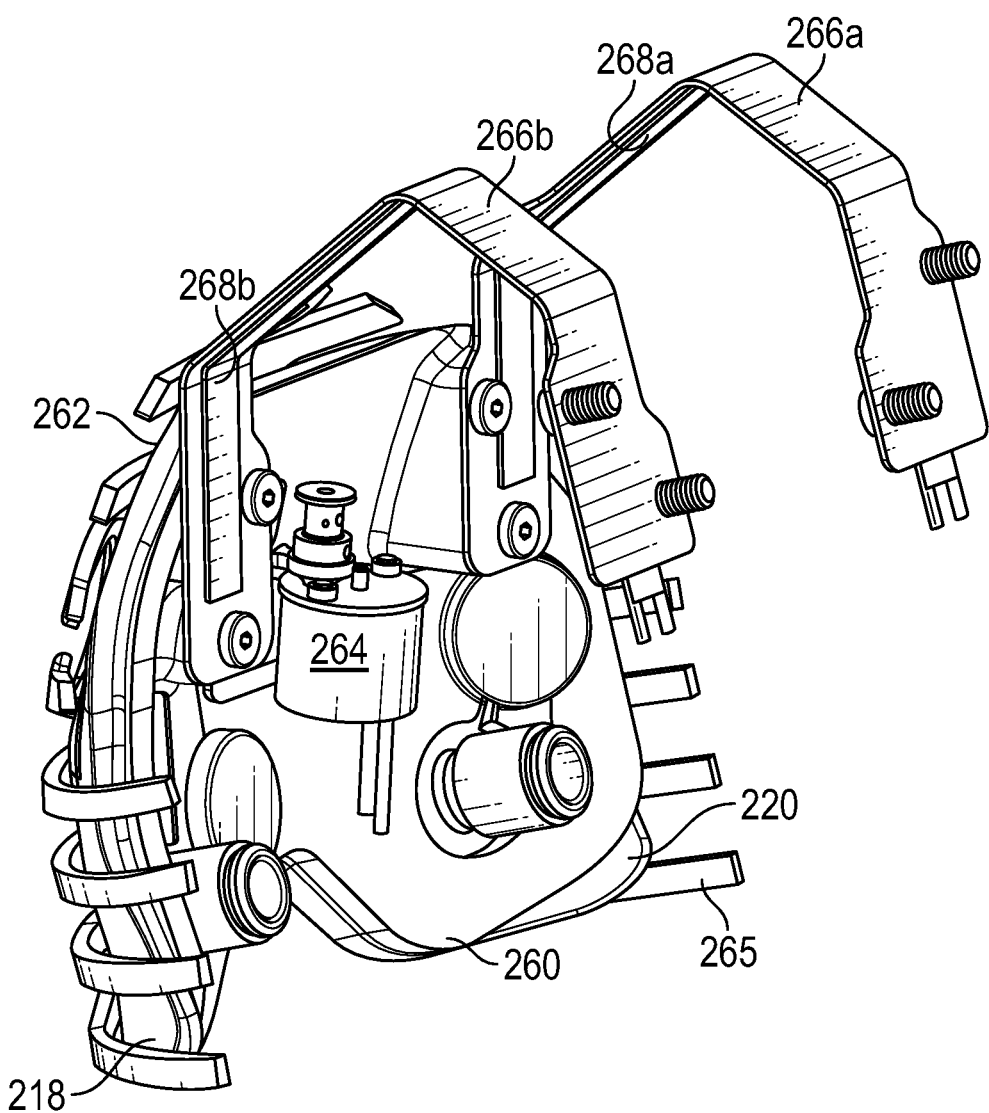
FIG. 36 is a rear perspective view of the simulated lungs of FIGS. 25 and 35, according to an exemplary embodiment.

In an exemplary embodiment, as illustrated in FIGS. 35 and 36, the simulated left and right lungs 218 and 220 form part of a lung compliance assembly 258. The lung compliance assembly 258 includes a backing plate 260, a pressure plate 262, and a compliance motor 264. The simulated left and right lungs 218 and 220 are trapped between the backing plate 260 and the pressure plate 262. The compliance motor 264 is connected to the backing plate 260 to actuate a compliance actuation line (not shown), which compliance actuation line is routed through the backing plate 260 and connected to the pressure plate 262. This actuation of the compliance actuation line adjusts the clamping force exerted by the pressure plate 262 on the simulated left and right lungs 218 and 220 to simulate the anatomical and physiological phenomena associated with the clinical presentation of lung compliance and its related complications. The lung compliance assembly 258 also includes simulated ribs 265 operably coupled to the pressure plate 262 to simulate the look and feel of a patient's ribs. In addition, connected to the backing plate 260 of the lung compliance assembly 258 is a chest deflection assembly 264 including a pair of leaf springs 266a and 266b. The leaf springs 266a and 266b include flex sensors 268a and 268b, respectively, contoured and affixed thereto. The leaf springs 266a and 266b are also connected to the back plate 82 of the upper torso bracket 78. In operation, the leaf springs 266a and 266b enable deflection of the lung compliance assembly 258 relative to the back plate 82 of the upper torso bracket 78, which deflection is measured by the flex sensors 268a and 268b. In this manner, the leaf springs 266a and 266b simulates the chest deflection of a patient without occupying the area behind the backing plate 260.

Figure 37:
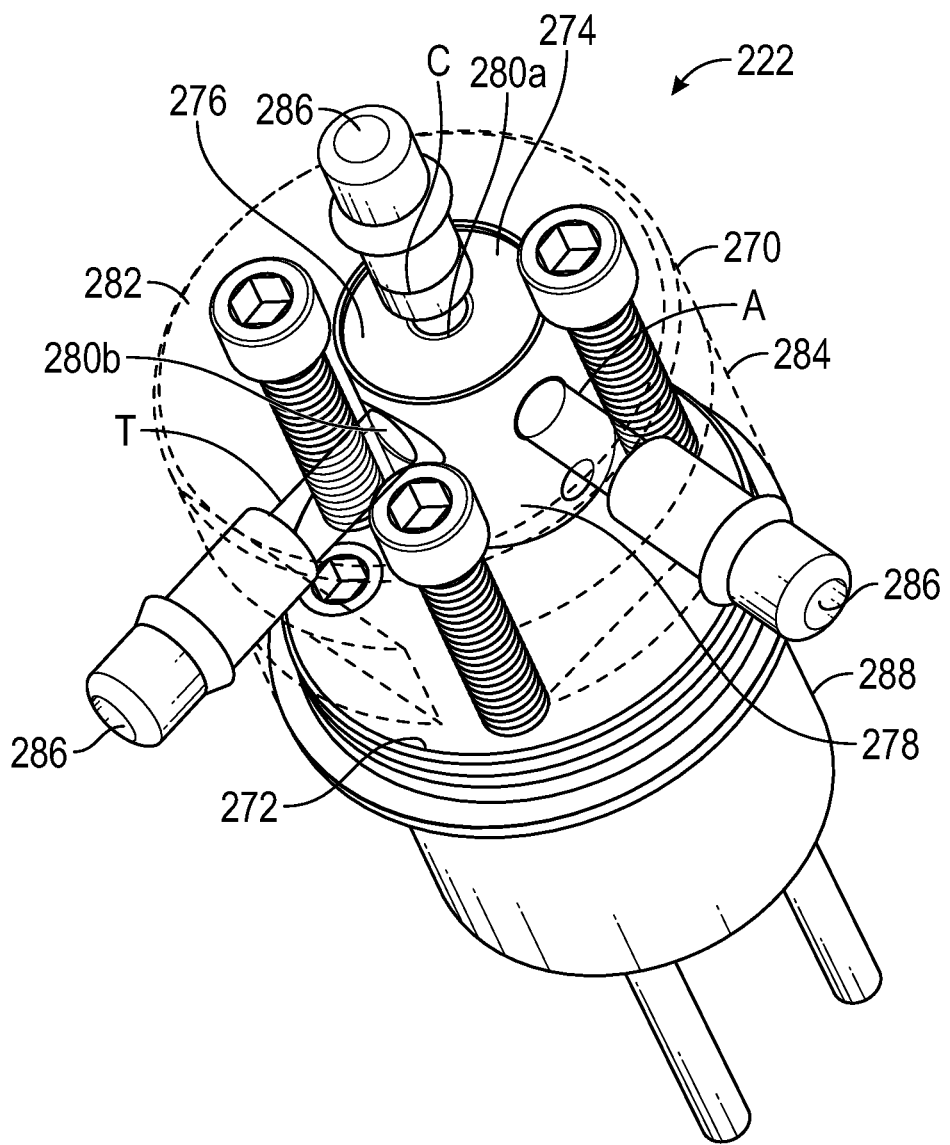
FIG. 37 is a perspective view of the airway valve of FIG. 25, according to an exemplary embodiment.

In an exemplary embodiment, as illustrated in FIG. 37, the airway valve 222 includes a valve body 270, a valve lid 272, and a valve rotor 274. The valve rotor 274 is generally cylindrical and includes an end face 276 and a curved side surface 278 having intersecting passageways 280a and 280b, respectively, formed therethrough. The valve body 270 is generally cylindrical and includes an end face 282 having the airway port C formed therethrough, and a curved side surface 284 having the airway ports T and A formed therethrough. The airway ports C, T, and A each include a fitting 286. The valve lid 272 is connected to the valve body 270, opposite the end face 282, to encase the valve rotor 274. A valve motor 288 is incorporated into the valve lid 272 and operably coupled to the valve rotor 274 via a motor coupling (not shown). The circumferential position of the valve rotor 274 relative to the valve body 270 is controlled by the valve motor 288. The passageways 280a and 280b of the valve rotor 274 and the airway ports C, T, and A of the valve body 270 are positioned so that the airway valve 222 is actuable, via rotation of the valve rotor 274, between the airway configuration in which the airway port A is in communication with the airway port C, and an abdominal configuration in which the airway port C is in communication with the airway port T. More particularly, in the airway configuration, the airway port A is in communication with the airway port C via the intersecting passageways 280a and 280b of the valve rotor 274. Similarly, in the abdominal configuration, the airway port C is in communication with the airway port T via the intersecting passageways 280a and 280b of the valve rotor 274.

Figure 38:
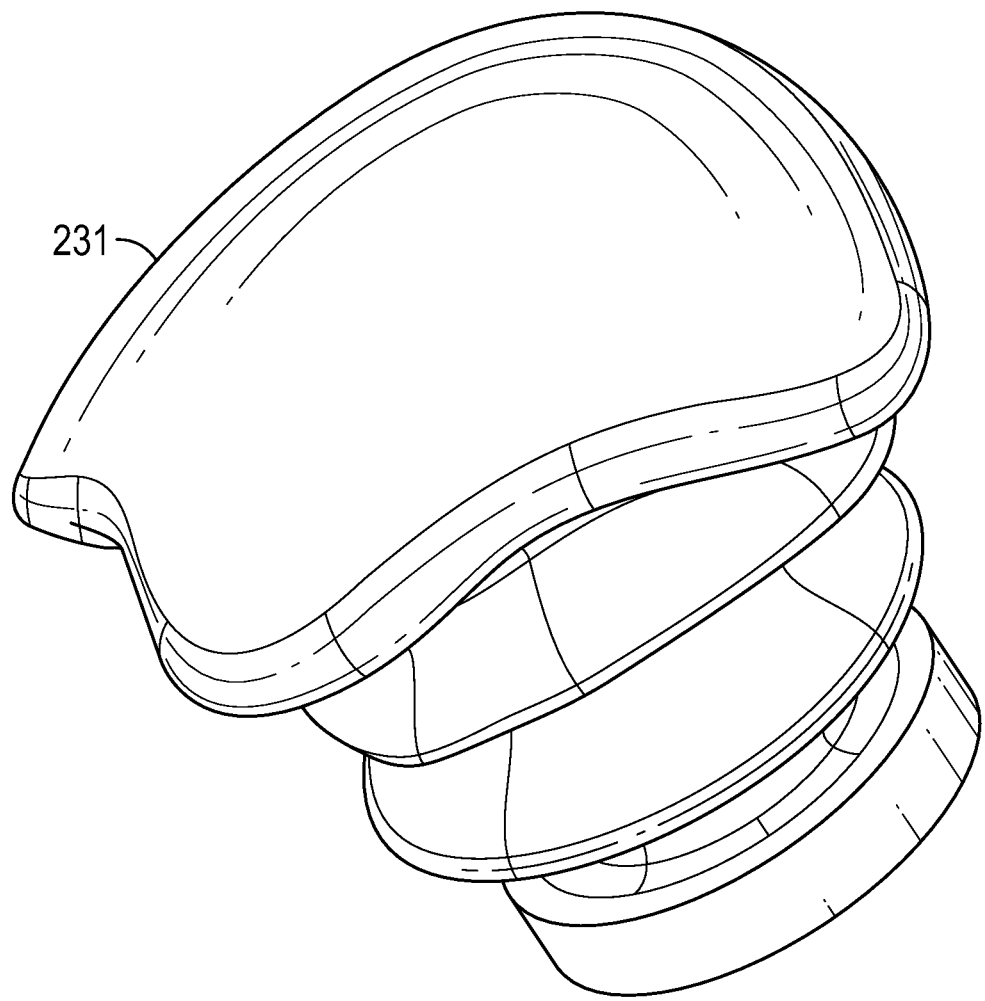
FIG. 38 is a perspective view of the abdominal expansion bag of FIG. 25, according to an exemplary embodiment.
Figure 39:
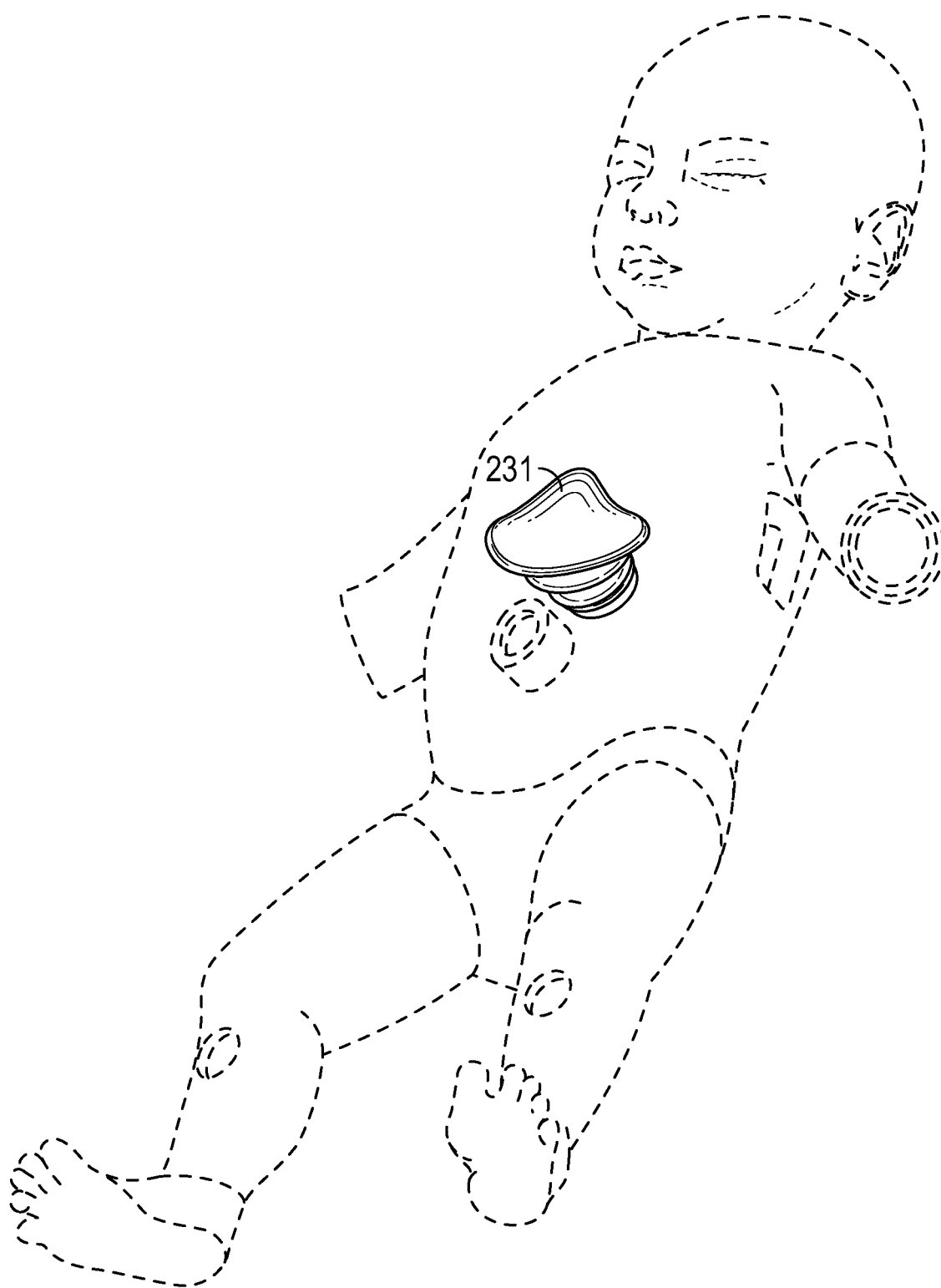
FIG. 39 is a perspective view of the abdominal expansion bag of FIG. 25 positioned in the patient simulator system of FIG. 1, according to an exemplary embodiment.
Figure 40:
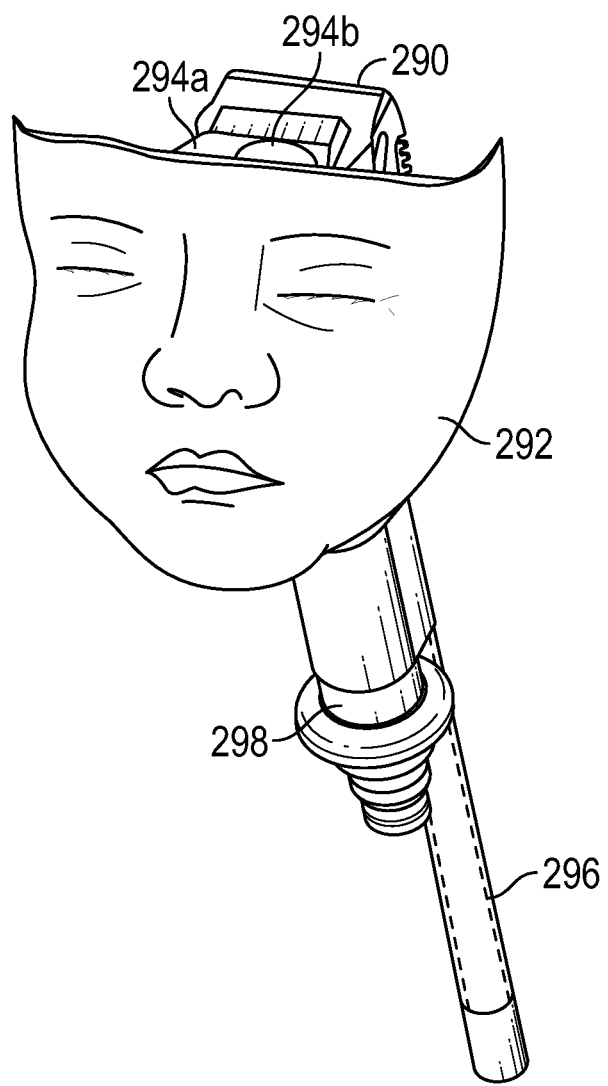
FIG. 40 is a front perspective view of the airway system of FIG. 25, according to an exemplary embodiment.
Figure 41:
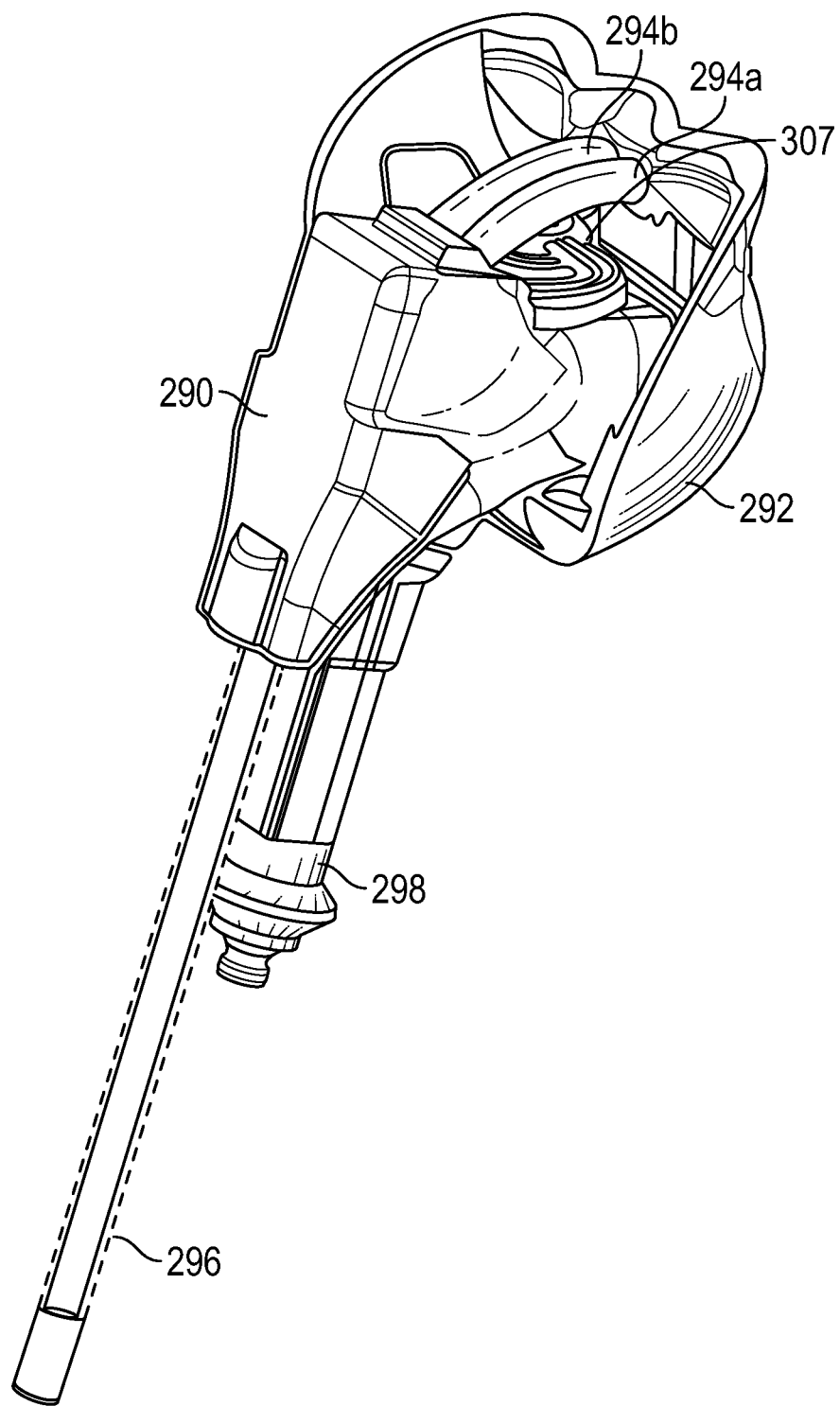
FIG. 41 is a rear perspective view of the airway system of FIGS. 25 and 40, according to an exemplary embodiment.
Figure 42:
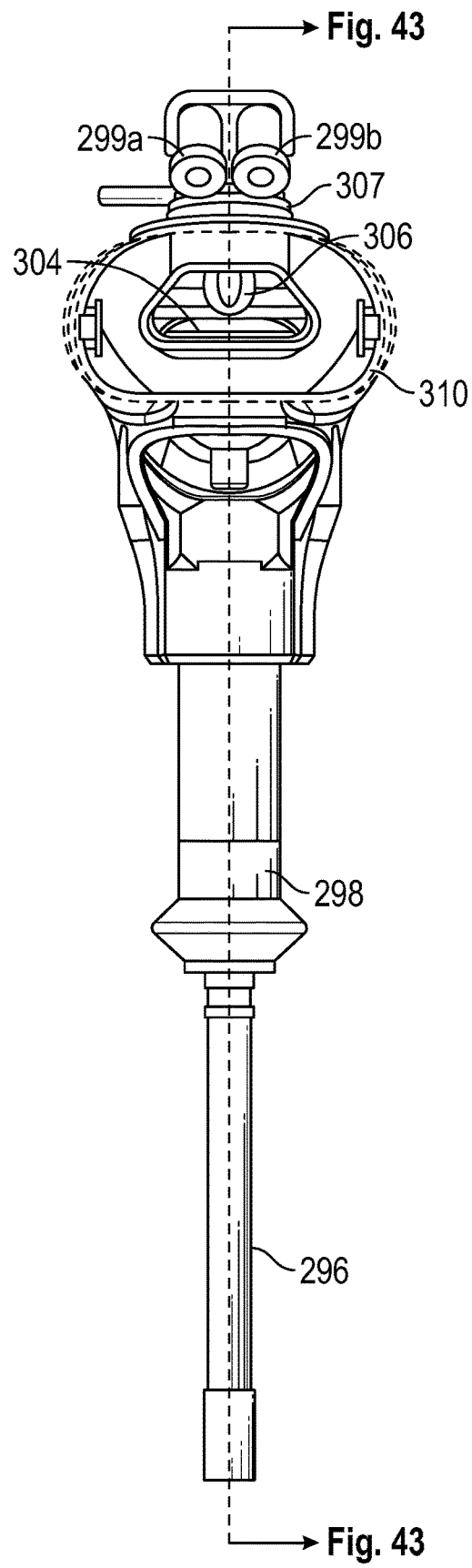
FIG. 42 is a front elevational view of the airway system of FIGS. 25, 40, and 41, according to an exemplary embodiment.
Figure 43:
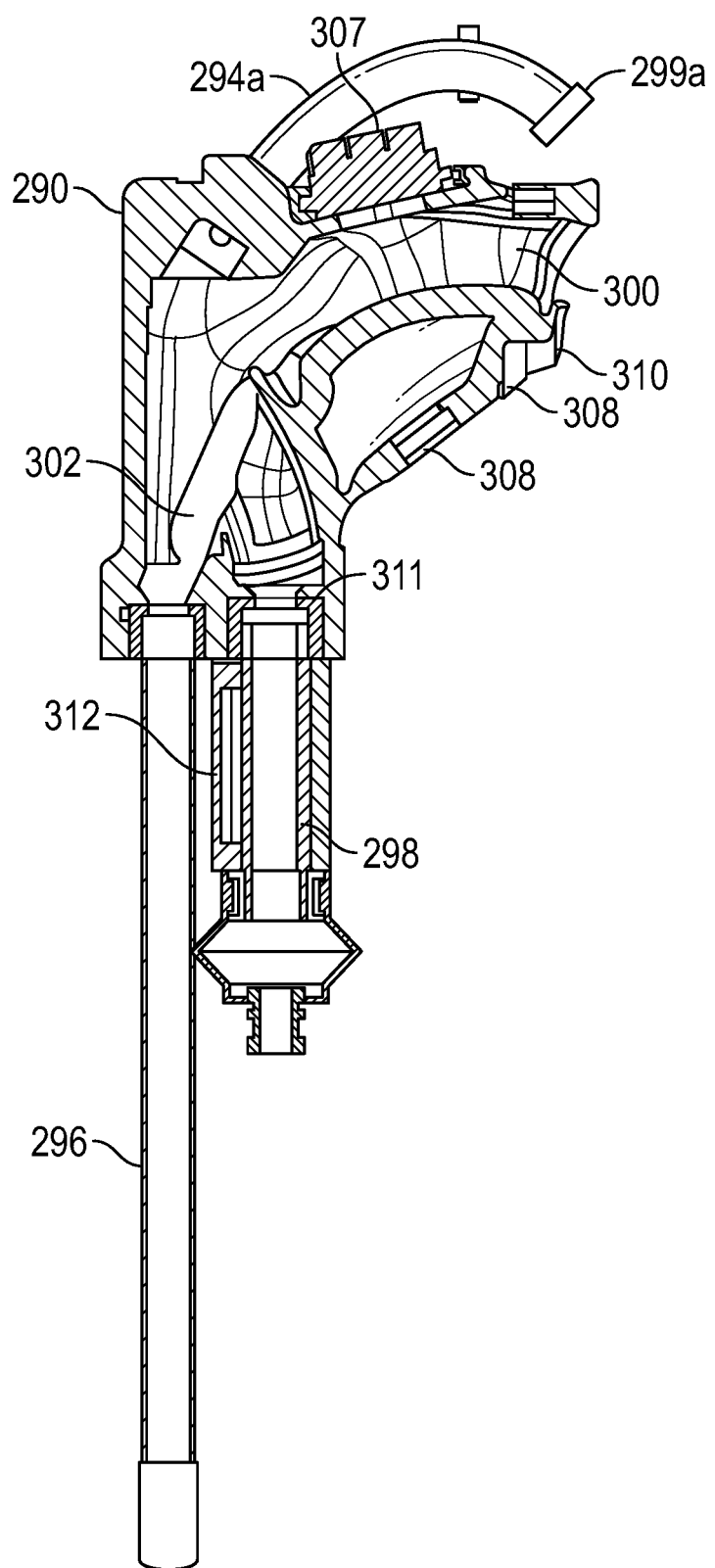
FIG. 43 is a cross-sectional view of the airway system of FIGS. 25 and 40-42, according to an exemplary embodiment.
Figure 44:
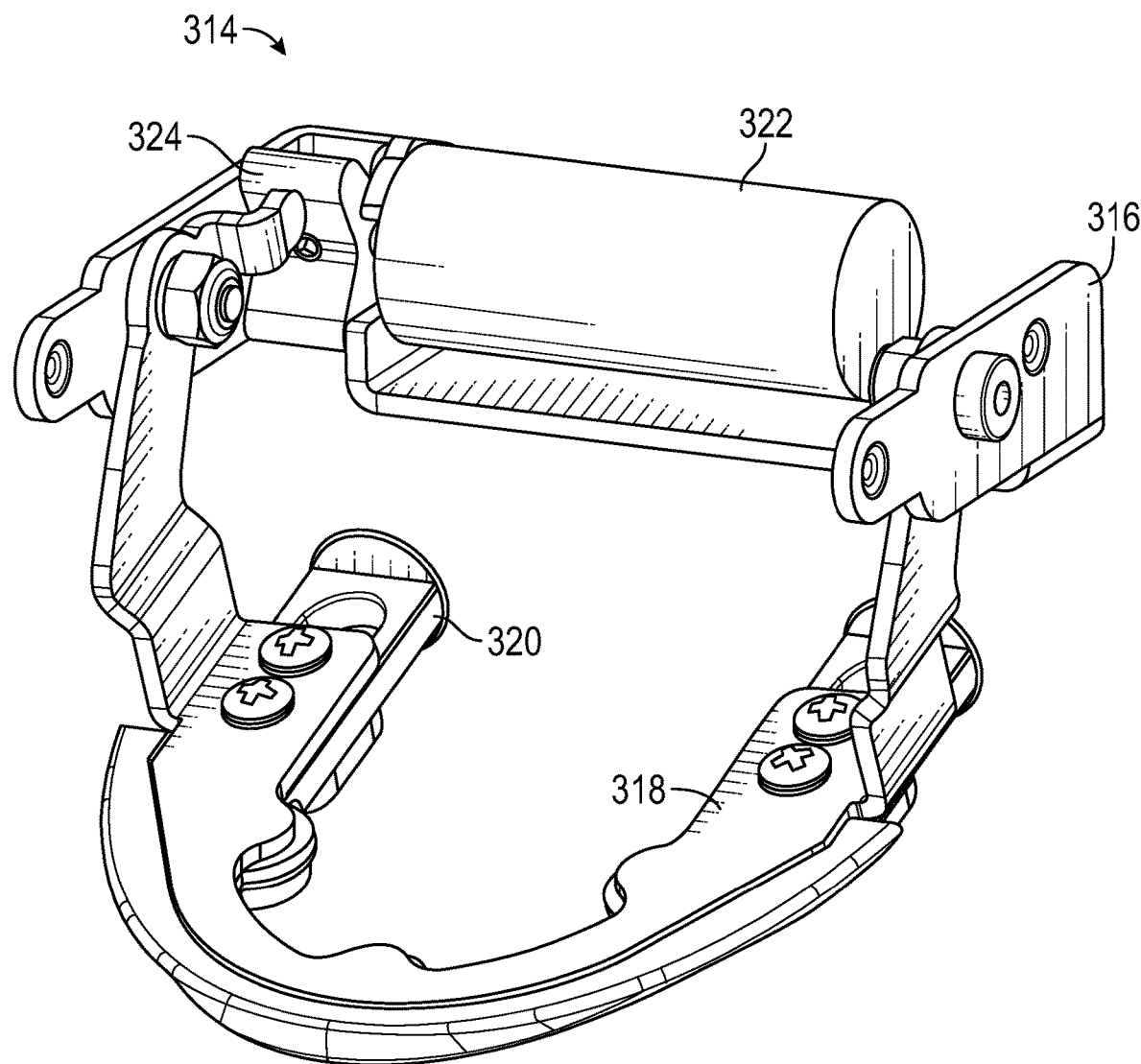
FIG. 44 is a perspective view of a mandible assembly for use with the simulated head of FIG. 1, the mandible assembly including a cheek bracket, a jaw bracket, a sliding mandible, a drive motor, and a double-lobed drive cam, according to an exemplary embodiment.
Figure 45:
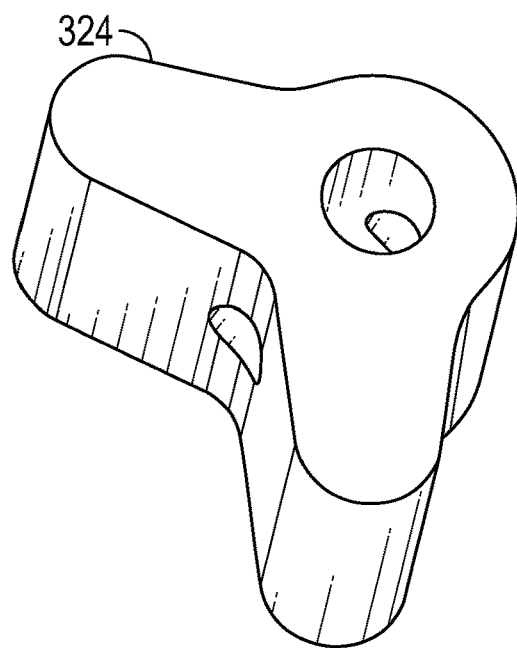
FIG. 45 is a perspective view of the double-lobed drive cam of FIG. 44, according to an exemplary embodiment.
Figure 46:
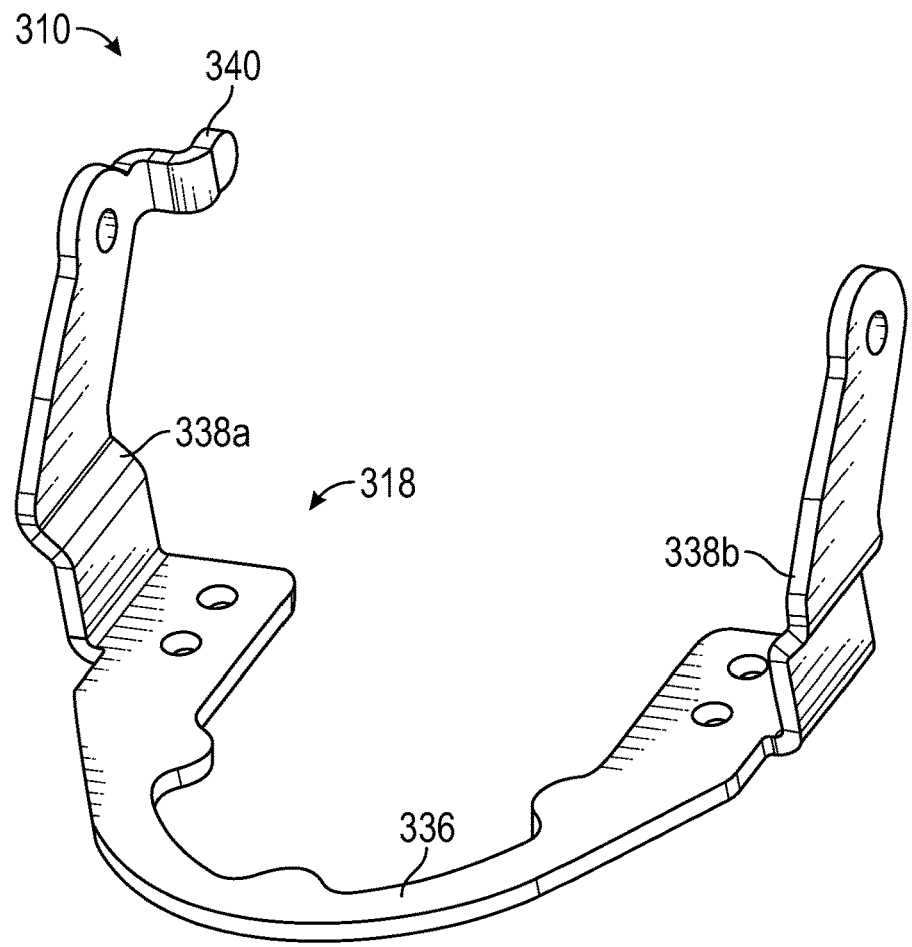
FIG. 46 is a perspective view of the jaw bracket of FIG. 44, according to an exemplary embodiment.
Figure 47:
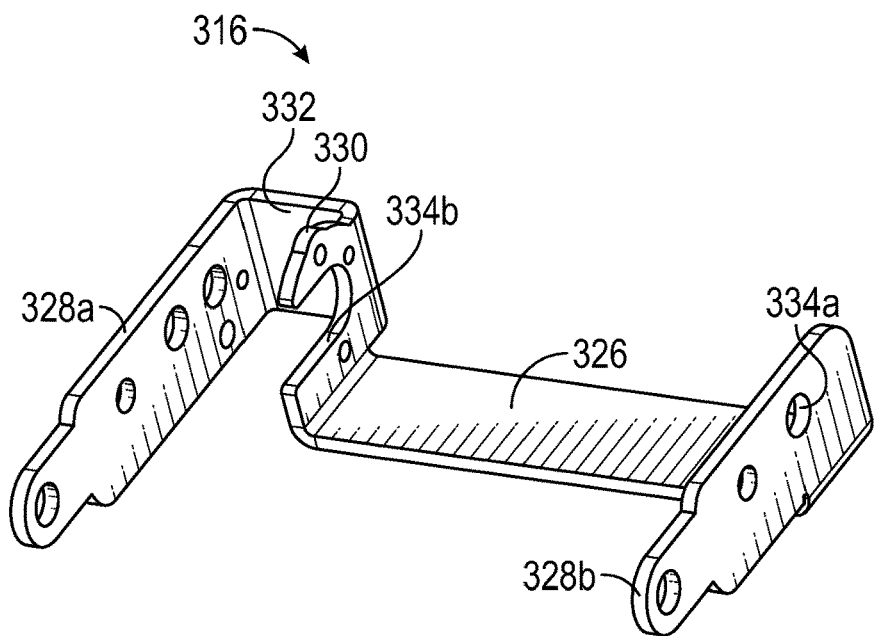
FIG. 47 is a perspective view of the cheek bracket of FIG. 44, according to an exemplary embodiment.
Figure 48:
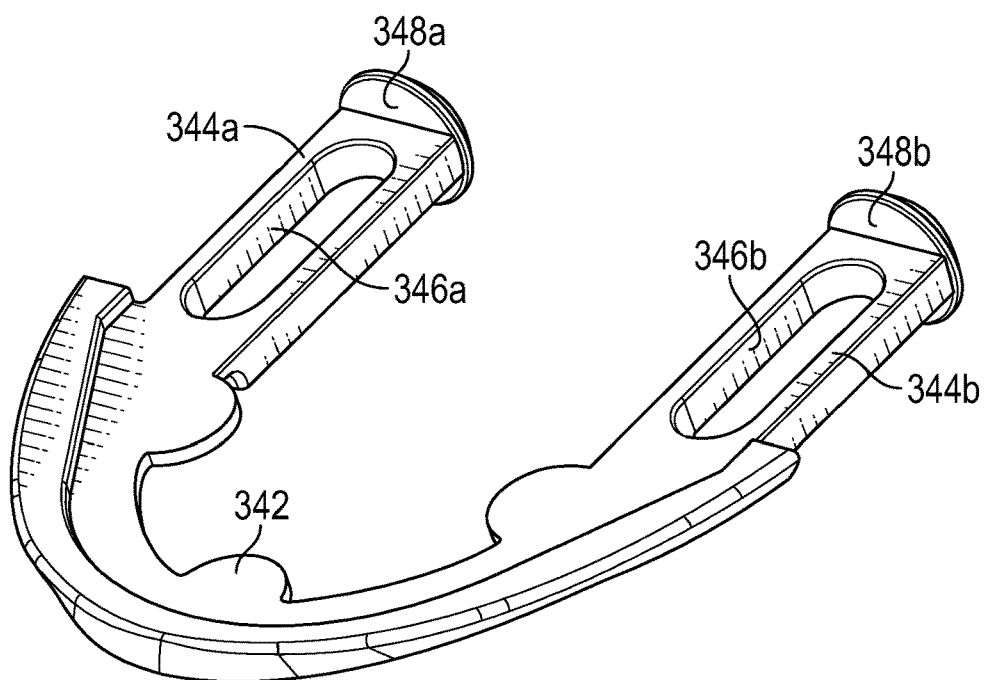
FIG. 48 is a perspective view of the sliding mandible of FIG. 44, according to an exemplary embodiment.
Figure 49:
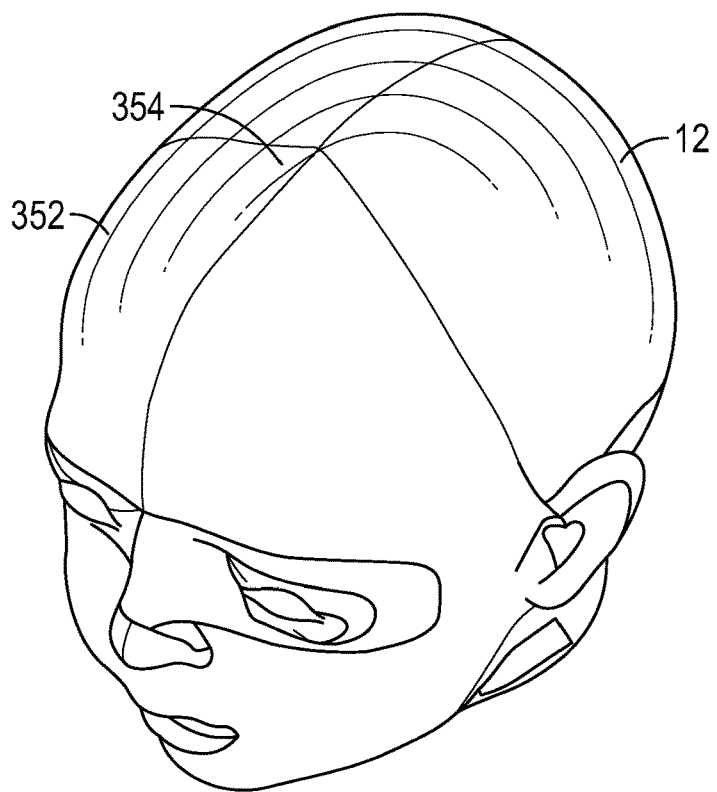
FIG. 49 is a perspective view of the simulated head of FIG. 1 including an endoskeleton skull and a skin layer into which a simulated fontanelle is incorporated, according to an exemplary embodiment.
Figure 50:
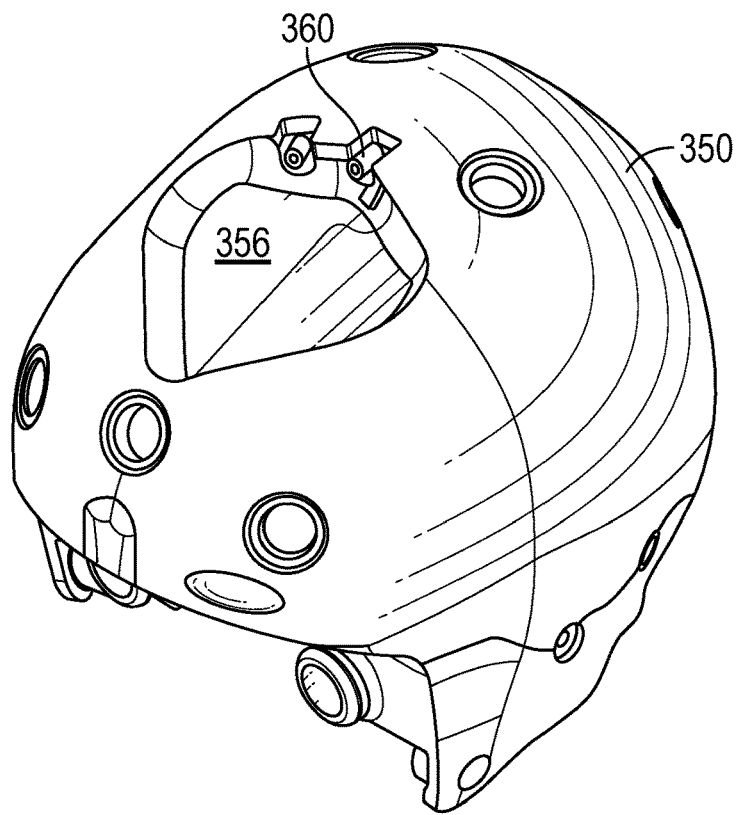
FIG. 50 is a perspective view of the endoskeleton skull of FIG. 49, according to an exemplary embodiment.
Figure 51:
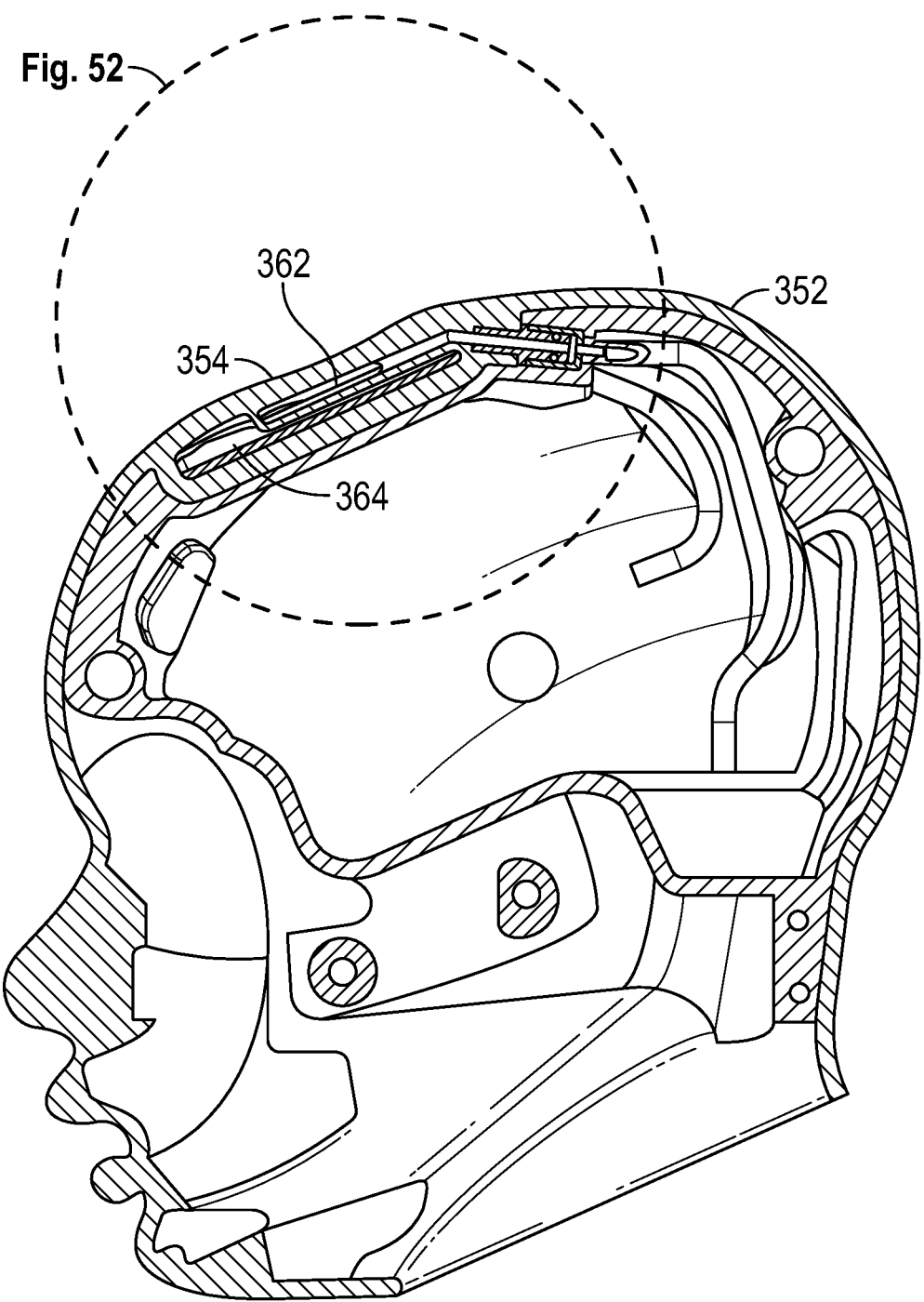
FIG. 51 is a cross sectional view of the simulated head of FIG. 49, according to an exemplary embodiment.

In an exemplary embodiment, as illustrated in FIGS. 38 and 39, the abdominal expansion bag 231 simulates the retraction and distention of the abdominal cavity. When used in combination, the abdominal expansion bag 231 and the breathing pump 214 enable precise control of breathing amplitude and frequency, along with all of the essential medical and physiological phenomena associated with a patient's abdomen. The position of the abdominal expansion bag 231 the patient simulator system 10 is shown most clearly in FIG. 39. In several exemplary embodiments, at least a portion of the abdominal expansion bag 231 extends within the empty space 159 defined by the lower torso bracket 151.

In an exemplary embodiment, as illustrated in FIGS. 40-43, the airway system 232 includes an airway unit 290, a skin layer 292, nose tubes 294a and 294b, an esophagus tube 296, and a trachea tube 298. The skin layer 292 is formed to simulate a patient's face (including simulated eyelids, nostrils, cheeks, and lips) and is operably coupled to the airway unit 290 and the nose tubes 294a and 294b. The nose tubes 294a and 294b are connected to the simulated nostrils of the skin layer 292 via a pair of nose tube bushings 299a and 299b. In several exemplary embodiments, the skin layer 292 is, includes, or is part of the simulated skin 22 of the patient simulator system 10. The airway unit 290 includes a mouth cavity 300 and an internal airway 302. The mouth cavity 300 and the internal airway 302 include anatomically correct simulated features, such as, for example, a simulated tongue 304, a simulated epiglottis 306, and simulated vocal cords (not shown). Additionally, a speaker 307 is operably coupled to the airway unit 190 and communicates audibly into the mouth cavity 300 to simulate a patient's vocal sounds. Operably coupled to the exterior of the airway unit 290 adjacent the mouth cavity 300 are light-emitting diodes (LEDs) 308 and a transparent (or semi-transparent) overmold 310 positioned between the LEDs 308 and the skin layer 292. The transparent overmold 310 diffuses light beneath the skin layer 292 (e.g., the simulated lips and cheeks) from the LEDs 308 to simulate the various states of a patient's face, including, for example, cyanosis, jaundice, paleness, and redness.

The esophagus tube 296 is operably coupled to the airway unit 290 and communicates with the internal airway 302. Similarly, the trachea tube 298 is operably coupled to the airway unit 290, adjacent the esophagus tube 296, and communicates with the internal airway 302. Moreover, the trachea tube 298 is operably coupled to the simulated respiratory system 212, and communicates with the airway valve 222 and the leg expansion bag(s) 182. An O-ring 311 is sealingly engaged between the trachea tube 298 and the airway unit 290 to facilitate an airtight seal with various tracheal intubation devices. A trachea tubing depth sensor 312 is operably coupled to the trachea tube 298 to ensure proper execution of various intratracheal training procedures. In addition, the nose tubes 294a and 294b are operably coupled to the airway unit 290 and communicate with the internal airway 302, opposite the esophagus tube 296 and the trachea tube 298.

In several exemplary embodiments, the mouth cavity 300 and the internal airway 302 are shaped to facilitate a training procedure for the insertion and placement of a laryngeal mask airway adjacent the trachea tube 298 and the esophagus tube 296. In several exemplary embodiments, the nose tubes 294a and 294b and the internal airway 302 are shaped to facilitate a training procedure for nasotracheal intubation. In several exemplary embodiments, the nose tubes 294a and 294b and the internal airway 302 are shaped to facilitate a training procedure for the insertion and placement of a nasogastric feeding tube. In several exemplary embodiments, the simulated respiratory system 212 and the airway system 232, in combination, enable realistic pulmonary feedback during various training procedures, such as, for example, a training procedure for endotracheal intubation, a training procedure for a valve bag mask ventilation, or another training procedure discussed herein.

In an exemplary embodiment, as illustrated in FIGS. 44-48, the simulated head 12 of the patient simulator system 10 includes a mandible assembly 314 operably coupled to the skin layer 292 and configured to open and close the simulated lips. The mandible assembly 314 includes a cheek bracket 316, a jaw bracket 318, a sliding mandible 320, a drive motor 322, and a double-lobed drive cam 324. The cheek bracket 316 includes a base plate 326, cheek plates 328a and 328b, a hook plate 330, and a back plate 332. The cheek plate 328b and the hook plate 330 extend transversely from opposing ends of the base plate 326 and define mounts 334a and 334b, respectively, to which the drive motor 322 is operably coupled. The back plate 332 extends transversely from the hook plate 330 in a direction opposite the base plate 326, and the cheek plate 328a extends transversely from the back plate 332. In combination, the hook plate 330, the back plate 332, and the cheek plate 328a define a space in which the double-lobed drive cam 324 extends. The hook plate 330 and the cheek plates 328a and 328b extend in parallel-spaced planes, and the back plate 332 and the base plate 326 extend in perpendicular-spaced planes.

The jaw bracket 318 includes a base plate 336 and side plates 338a and 338b extending transversely from opposing ends of the base plate 336. The side plates 338a and 338b are pivotably coupled to the cheek plates 328a and 328b of the cheek bracket 316. Moreover, the side plate 338a includes an integrated lever 340 operably coupled to the double-lobed drive cam 324. As a result, the rotation of the double-lobed drive cam 324 by the drive motor 322 pivots the jaw bracket 318 about the pivotable connection between the side plates 338a and 338b and the cheek plates 328a and 328b. The double-lobed drive cam 324 is shaped to enable uninhibited manipulation of the jaw bracket 318 when in the center (or neutral) position.

The sliding mandible 320 is a generally U-shaped component including a mandible body 342 and slides 344a and 344b connected to opposing ends of the mandible body 342. The slides 344a and 344b include slots 346a and 346b, respectively. Moreover, domed bumpers 348a and 348b are connected to the slides 344a and 344b, respectively, opposite the mandible body 342. The domed bumpers 348a and 348b serve as anatomical landmarks within the patient simulator system 10's simulated head 12. The sliding mandible 320 is connected to the jaw bracket 318 via fasteners extending through the slots 346a and 346b. As a result, the sliding mandible 320 is moveable relative to the jaw bracket 318 between a retruded position in which the base plate 336 of the jaw bracket 318 complementarily engages the mandible body 342, and a protruded position in which the domed bumpers 348a and 348b engage the opposing ends of the base plate 336. In this manner, the jaw bracket 318 and the sliding mandible 320 are together operable to simulate the form and function of a patient's jaw. The sliding mandible 320 is also connected to the skin layer 292 to further enhance the skin layer 292's simulation of a patient's face.

In an exemplary embodiment, as illustrated in FIGS. 49-52, the simulated head 12 of the patient simulator system 10 further includes an endoskeleton skull 350 and a skin layer 352 into which a simulated fontanelle 354 is incorporated. In several exemplary embodiments, the simulated fontanelle 354 is integrally formed with the skin layer 352. Moreover, in several exemplary embodiments, the skin layer 352 is, includes, or is part of the simulated skin 22 of the patient simulator system 10. The endoskeleton skull 350 includes an indented fontanelle region 356 generally in the shape of a patient's fontanelle. Extending through the endoskeleton skull 350 adjacent the indented fontanelle region 356 are a fontanelle fitting 358 and a pulse fitting 360. The simulated fontanelle 354 includes a pulse bladder 362 and a fontanelle bladder 364 formed in the skin layer 352. The fontanelle bladder 364 extends within the indented fontanelle region 356 of the endoskeleton skull 350, and the pulse bladder 362 extends adjacent the fontanelle bladder 364. The pulse bladder 362 is operably coupled to the pulse fitting 360, and communicates with the simulated circulatory system (not shown) to receive the pneumatic or hydraulic pulse. The fontanelle bladder 364 is operably coupled to the fontanelle fitting 358, and communicates with the simulated respiratory system 212 to receive either positive or negative (vacuum) pressure. This positive or negative (vacuum) pressure produces either a swollen or sunken state in the simulated fontanelle 354.

Figure 52:
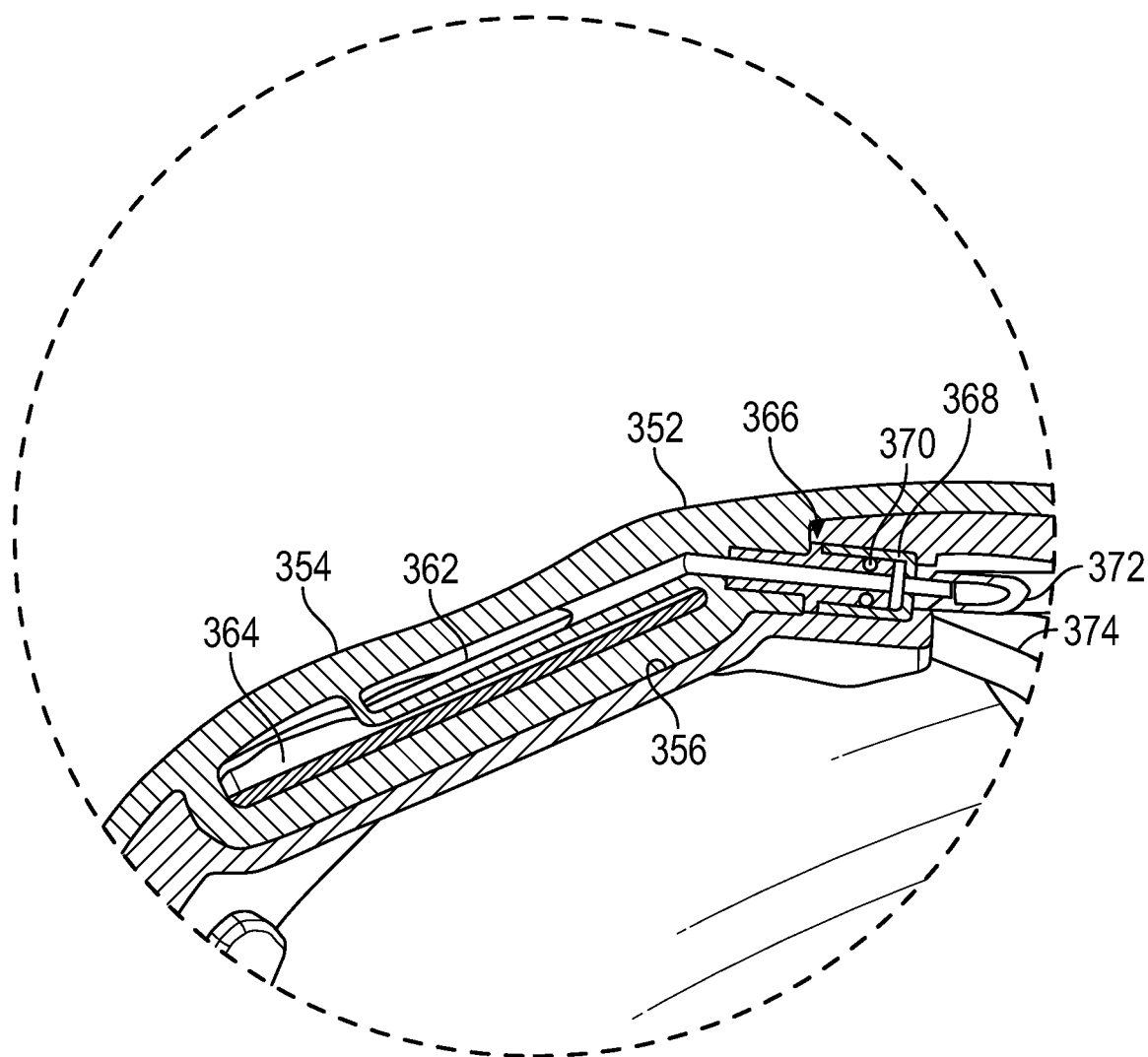
FIG. 52 is an enlarged view of the simulated head of FIG. 51, according to an exemplary embodiment.

In several exemplary embodiments, the fontanelle fitting 358 and the pulse fitting 360 are substantially identical to one another, and, therefore, in connection with FIG. 52, only the pulse fitting 360 will be described in detail below; however the description below applies to both the fontanelle fitting 358 and the pulse fitting 360. Turning to FIG. 52, the pulse fitting 360 includes a male coupling 366 connected to the skin layer 352 and a female coupling 368 connected to the endoskeleton skull 350. An O-ring 370 extends within an annular groove on the male coupling 366, opposite the skin layer 352. The female coupling 368 receives the male coupling 366 and is sealingly engaged by the O-ring 370. Operably coupled to the female coupling 368, opposite the male coupling 366, is a pulse air supply line 372 that communicates with the simulated circulatory system to receive the pneumatic or hydraulic pulse. In a similar manner, a fontanelle air supply line 374 is connected to the female coupling (not visible in FIG. 52) of the fontanelle fitting 358, and communicates with the simulated respiratory system 212 to receive either the positive or negative (vacuum) pressure.

The present disclosure introduces a patient simulator, including a simulated respiratory system and a simulated airway system, the simulated respiratory system including a lung valve; a first simulated lung in communication with the lung valve; and a breathing pump including a cylinder and a piston dividing the cylinder into first and second chambers, the first chamber being in communication with the lung valve via at least a first flow path, the second chamber being in communication with the lung valve via at least a second flow path, and the piston being adapted to reciprocate within the cylinder; and the simulated airway system being configured to be in communication with the second chamber of the breathing pump via at least a third flow path. In several exemplary embodiments, the patient simulator further includes an airway valve including first, second, and third ports, and being actuable between an airway configuration, in which the first port is in communication with the third port, but not the second port, and an abdominal configuration, in which the first port is in communication with the second port, but not the third port; wherein the first port is in communication with the second chamber of the breathing pump; wherein the third port is in communication with the simulated airway system; and wherein, when the airway valve is in the airway configuration, the first and third ports form part of the third flow path. In several exemplary embodiments, the second port of the airway valve is in communication with an abdominal expansion bag of the patient simulator so that when the airway valve is in the abdominal configuration: each stroke of the piston in a first direction produces a pressure decrease in the abdominal expansion bag and forces air from the first chamber of the breathing pump into the first simulated lung via at least the first flow path, and each stroke of the piston in a second direction, which is opposite the first direction, produces a pressure increase in the abdominal expansion bag and draws air out of the first simulated lung and into the first chamber of the breathing pump via at least the first flow path; and wherein the increase and decrease of pressure in the abdominal expansion bag simulates respiratory distress in a human patient. In several exemplary embodiments, the lung valve includes first, second, and third ports, and is actuable between a spontaneous breathing configuration, in which the first port is in communication with the second port, and an assisted breathing configuration, in which both of the first and third ports are in communication with the second port; wherein the first chamber of the breathing pump is in communication with the first port via at least the first flow path; wherein the first simulated lung is in communication with the second port; and wherein the second chamber of the breathing pump is in communication with the third port via at least the second flow path. In several exemplary embodiments, the lung valve further includes a fourth port arranged so that, in the spontaneous breathing configuration, the first port is in communication with one, or both, of the second port and the fourth port, and, in the assisted breathing configuration, both of the first and third ports are in communication with one, or both, of the second and fourth ports; and wherein the simulated respiratory system further includes a second simulated lung in communication with the fourth port. In several exemplary embodiments, at least respective portions of the second and third flow paths are in communication with each other and the second chamber of the breathing pump. In several exemplary embodiments, when the lung valve is in the spontaneous breathing configuration and the simulated airway system is in communication with the second chamber of the breathing pump via at least the third flow path: each stroke of the piston in a first direction forces air from the first chamber of the breathing pump into the first simulated lung via at least the first flow path, and produces a pressure decrease in the airway system to simulate inhalation of a human patient's breath; and each stroke of the piston in a second direction, which is opposite the first direction, draws air out of the first simulated lung into the first chamber of the breathing pump via at least the first flow path, and produces a pressure increase in the airway system to simulate exhalation of the human patient's breath. In several exemplary embodiments, when the lung valve is in the assisted breathing configuration and the simulated airway system is in communication with the second chamber of the breathing pump via at least the third flow path: each stroke of the piston in a first direction produces a pressure decrease in the airway system while permitting air to escape from the third port of the lung valve to the airway system via at least respective portions of the second and third flow paths; and each stroke of the piston in a second direction, which is opposite the first direction, produces a pressure increase in the airway system while permitting air to escape from the airway system to the third port of the lung valve via at least respective portions of the second and third flow paths; and the escape of air from the third port of the lung valve to the airway system, and vice versa, during the respective strokes of the piston in the first and second directions, produces a pressure fluctuation in the airway system that simulates a human patient gasping for breath. In several exemplary embodiments, at least a portion of the second flow path is smaller in diameter than the first flow path to facilitate said pressure fluctuation. In several exemplary embodiments, a mechanical ventilator is operably coupleable to the simulated airway system and configurable to sense said pressure fluctuation.

The present disclosure also introduces a method, including simulating, using a patient simulator, a human patient's breathing pattern, the patient simulator including a simulated respiratory system and a simulated airway system, the simulated respiratory system including a lung valve, a first simulated lung in communication with the lung valve, and a breathing pump including a cylinder and a piston dividing the cylinder into first and second chambers, the first chamber being in communication with the lung valve via at least a first flow path, and the second chamber being in communication with the lung valve via at least a second flow path; and the simulated airway system being configured to be in communication with the second chamber of the breathing pump via at least a third flow path; wherein simulating, using the patient simulator, the human patient's breathing pattern includes reciprocating the piston within the cylinder. In several exemplary embodiments, the method further includes actuating an airway valve of the patient simulator to an airway configuration, the airway valve including a first port in communication with the second chamber of the breathing pump, a second port, and a third port in communication with the simulated airway system; wherein, when the airway valve is in the airway configuration, the first port is in communication with the third port, but not the second port, so that the first and third ports form part of the third flow path. In several exemplary embodiments, the method further includes simulating, using the patient simulator, respiratory distress within the human patient; wherein the second port of the airway valve is in communication with an abdominal expansion bag of the patient simulator; and wherein simulating, using the patient simulator, respiratory distress within the human patient includes: stroking, when the airway valve is in the abdominal configuration, the piston in a first direction to produce a pressure decrease in the abdominal expansion bag and force air from the first chamber of the breathing pump into the first simulated lung via at least the first flow path; and stroking, when the airway valve is in the abdominal configuration, the piston in a second direction, which is opposite the first direction, to produce a pressure increase in the abdominal expansion bag and draw air out of the first simulated lung and into the first chamber of the breathing pump via at least the first flow path. In several exemplary embodiments, the lung valve includes first, second, and third ports, the first chamber of the breathing pump being in communication with the first port via at least the first flow path, the first simulated lung being in communication with the second port, and the second chamber of the breathing pump being in communication with the third port via at least the second flow path; and the method further includes actuating the lung valve between a spontaneous breathing configuration, in which the first port is in communication with the second port, and an assisted breathing configuration, in which both of the first and third ports are in communication with the second port. In several exemplary embodiments, the lung valve further includes a fourth port arranged so that, in the spontaneous breathing configuration, the first port is in communication with one, or both, of the second port and the fourth port, and, in the assisted breathing configuration, both of the first and third ports are in communication with one, or both, of the second and fourth ports; and the simulated respiratory system further includes a second simulated lung in communication with the fourth port. In several exemplary embodiments, at least respective portions of the second and third flow paths are in communication with each other and the second chamber of the breathing pump. In several exemplary embodiments, simulating, using the patient simulator, the human patient's breathing pattern includes: stroking, when lung valve is in the spontaneous breathing configuration and the simulated airway system is in communication with the second chamber of the breathing pump via at least the third flow path, the piston in a first direction to force air from the first chamber of the breathing pump into the first simulated lung via at least the first flow path, and produce a pressure decrease in the airway system to simulate inhalation of the human patient's breath; and stroking, when lung valve is in the spontaneous breathing configuration and the simulated airway system is in communication with the second chamber of the breathing pump via at least the third flow path, the piston in a second direction, which is opposite the first direction, to draw air out of the first simulated lung into the first chamber of the breathing pump via at least the first flow path, and produces a pressure increase in the airway system to simulate exhalation of the human patient's breath. In several exemplary embodiments, the method further includes producing, using the patient simulator, a pressure fluctuation in the airway system to simulate the human patient gasping for breath; wherein producing, using the patient simulator, the pressure fluctuation in the airway system to simulate the human patient gasping for breath includes: stroking the piston in a first direction to produce a pressure decrease in the airway system while permitting air to escape from the third port of the lung valve to the airway system via at least respective portions of the second and third flow paths; and stroking the piston in a second direction, which is opposite the first direction, to produce a pressure increase in the airway system while permitting air to escape from the airway system to the third port of the lung valve via at least respective portions of the second and third flow paths. In several exemplary embodiments, at least a portion of the second flow path is smaller in diameter than the first flow path to facilitate said pressure fluctuation. In several exemplary embodiments, the method further includes operably coupling a mechanical ventilator to the simulated airway system, the mechanical ventilator being configurable to sense said pressure fluctuation.

The present disclosure also introduces a patient simulator system including a simulated respiratory system, the simulated respiratory system including simulated left and right lungs, a lung valve, a breathing pump, an airway pump, an abdominal expansion bag, a leg expansion bag, and an airway system. In an exemplary embodiment, the breathing pump includes cylinder and a piston dividing the cylinder into first and second chambers, the piston being adapted to reciprocate in the cylinder. In an exemplary embodiment, the lung valve includes first, second, third, and fourth breathing ports, the first breathing port being in communication with the second chamber of the breathing pump via a first line, the second breathing port being in communication with both the airway valve and the first chamber of the breathing pump via a second line, and the third and fourth breathing ports being in communication with the simulated left and right lungs, respectively, wherein the second line is relatively smaller in diameter than the first line. In an exemplary embodiment, the lung valve is actuable between: a first breathing configuration in which the first breathing port is in communication with one or both of the third and fourth breathing ports; and a second breathing configuration in which both the first and second breathing ports are in communication with one or both of the third and fourth breathing ports.

The present disclosure also introduces a patient simulator system including a simulated torso, simulated arms, and simulated legs, the simulated torso including an upper torso bracket interconnecting the simulated arms, and a lower torso bracket interconnecting the simulated legs. In an exemplary embodiment, the simulated arms and the simulated legs are connected to the upper torso bracket and the lower torso bracket, respectively, via articulation joints, the articulation joints each including a clamp, a ball, and a clamp screw.

The present disclosure also introduces a patient simulator system including a simulated head, the simulated head including an endoskeleton skull and in skin layer into which a simulated fontanelle is incorporated. In an exemplary embodiment, the simulated fontanelle includes a pulse bladder and a fontanelle bladder formed in the skin layer. In an exemplary embodiment, the simulated skull includes an indented fontanelle region, a fontanelle fitting, and a pulse fitting, the fontanelle fitting and the pulse fitting each extending through the endoskeleton skull adjacent the indented fontanelle region. In an exemplary embodiment, the fontanelle bladder extends within the indented fontanelle region of the endoskeleton skull, is operably coupled to the fontanelle fitting, and communicates with a simulated respiratory system of the patient simulator system to receive either positive or negative (vacuum) pressure. In an exemplary embodiment, the pulse bladder extends adjacent the fontanelle bladder, is operably coupled to the pulse fitting, and communicates with a simulated circulatory system of the patient simulator system to receive a pneumatic or hydraulic pulse.

The present disclosure also introduces a simulated respiratory system for a patient simulator system according to one or more aspects of the present disclosure.

The present disclosure also introduces a lung valve according to one or more aspects of the present disclosure.

The present disclosure also introduces a breathing pump according to one or more aspects of the present disclosure.

The present disclosure also introduces an airway valve according to one or more aspects of the present disclosure.

The present disclosure also introduces an airway system according to one or more aspects of the present disclosure.

The present disclosure also introduces a method according to one or more aspects of the present disclosure.

The present disclosure also introduces a system according to one or more aspects of the present disclosure.

The present disclosure also introduces an apparatus according to one or more aspects of the present disclosure.

The present disclosure also introduces a kit according to one or more aspects of the present disclosure.

It is understood that variations may be made in the foregoing without departing from the scope of the present disclosure.

In various embodiments, the elements and teachings of the various embodiments may be combined in whole or in part in some or all of the various embodiments. In addition, one or more of the elements and teachings of the various embodiments may be omitted, at least in part, and/or combined, at least in part, with one or more of the other elements and teachings of the various embodiments.

In various embodiments, while different steps, processes, and procedures are described as appearing as distinct acts, one or more of the steps, one or more of the processes, and/or one or more of the procedures may also be performed in different orders, simultaneously and/or sequentially. In various embodiments, the steps, processes and/or procedures may be merged into one or more steps, processes and/or procedures.

In various embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

Although various embodiments have been described in detail above, the embodiments described are illustrative only and are not limiting, and those skilled in the art will readily appreciate that many other modifications, changes and/or substitutions are possible in the various embodiments without materially departing from the novel teachings and advantages of the present disclosure. Accordingly, all such modifications, changes, and/or substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the applicant not to invoke 35 U.S.C. § 112, paragraph 6 for any limitations of any of the claims herein, except for those in which the claim expressly uses the word "means" together with an associated function.

What is claimed is:

1. A patient simulator, comprising:
 a simulated respiratory system, comprising:
  a lung valve;
  a first simulated lung in communication with the lung valve; and
  a breathing pump including a cylinder and a piston dividing the cylinder into first and second chambers, the first chamber being in communication with the lung valve via at least a first flow path, the second chamber being in communication with the lung valve via at least a second flow path, and the piston being adapted to reciprocate within the cylinder; and
 a simulated airway system configured to be in communication with the second chamber of the breathing pump via at least a third flow path.

2. The patient simulator of claim 1, further comprising an airway valve including first, second, and third ports, and being actuable between an airway configuration, in which the first port is in communication with the third port, but not the second port, and an abdominal configuration, in which the first port is in communication with the second port, but not the third port;
  wherein the first port is in communication with the second chamber of the breathing pump;
  wherein the third port is in communication with the simulated airway system; and
  wherein, when the airway valve is in the airway configuration, the first and third ports form part of the third flow path.

3. The patient simulator of claim 2, wherein the second port of the airway valve is in communication with an abdominal expansion bag of the patient simulator so that, when the airway valve is in the abdominal configuration:
  each stroke of the piston in a first direction produces a pressure decrease in the abdominal expansion bag and forces air from the first chamber of the breathing pump into the first simulated lung via at least the first flow path; and
  each stroke of the piston in a second direction, which is opposite the first direction, produces a pressure increase in the abdominal expansion bag and draws air out of the first simulated lung and into the first chamber of the breathing pump via at least the first flow path; and
  wherein the increase and decrease of pressure in the abdominal expansion bag simulates respiratory distress in a human patient.

4. The patient simulator of claim 1, wherein the lung valve includes first, second, and third ports, and is actuable between a spontaneous breathing configuration, in which the first port is in communication with the second port, and an assisted breathing configuration, in which both of the first and third ports are in communication with the second port;
  wherein the first chamber of the breathing pump is in communication with the first port via at least the first flow path;
  wherein the first simulated lung is in communication with the second port; and
  wherein the second chamber of the breathing pump is in communication with the third port via at least the second flow path.

5. The patient simulator of claim 4, wherein the lung valve further includes a fourth port arranged so that, in the spontaneous breathing configuration, the first port is in communication with one, or both, of the second port and the fourth port, and, in the assisted breathing configuration, both of the first and third ports are in communication with one, or both, of the second and fourth ports; and
  wherein the simulated respiratory system further comprises a second simulated lung in communication with the fourth port.

6. The patient simulator of claim 4, wherein at least respective portions of the second and third flow paths are in communication with each other and the second chamber of the breathing pump.

7. The patient simulator of claim 4, wherein, when the lung valve is in the spontaneous breathing configuration and the simulated airway system is in communication with the second chamber of the breathing pump via at least the third flow path:
  each stroke of the piston in a first direction forces air from the first chamber of the breathing pump into the first simulated lung via at least the first flow path, and produces a pressure decrease in the airway system to simulate inhalation of a human patient's breath; and
  each stroke of the piston in a second direction, which is opposite the first direction, draws air out of the first simulated lung into the first chamber of the breathing pump via at least the first flow path, and produces a pressure increase in the airway system to simulate exhalation of the human patient's breath.

8. The patient simulator of claim 4, wherein, when the lung valve is in the assisted breathing configuration and the simulated airway system is in communication with the second chamber of the breathing pump via at least the third flow path:
  each stroke of the piston in a first direction produces a pressure decrease in the airway system while permitting air to escape from the third port of the lung valve to the airway system via at least respective portions of the second and third flow paths; and
  each stroke of the piston in a second direction, which is opposite the first direction, produces a pressure increase in the airway system while permitting air to escape from the airway system to the third port of the lung valve via at least respective portions of the second and third flow paths;
  and
  wherein the escape of air from the third port of the lung valve to the airway system, and vice versa, during the respective strokes of the piston in the first and second directions, produces a pressure fluctuation in the airway system that simulates a human patient gasping for breath.

9. The patient simulator of claim 8, wherein at least a portion of the second flow path is smaller in diameter than the first flow path to facilitate said pressure fluctuation.

10. The patient simulator of claim 8, wherein a mechanical ventilator is operably coupleable to the simulated airway system and configurable to sense said pressure fluctuation.

11. A method, comprising:
  simulating, using a patient simulator, a human patient's breathing pattern, the patient simulator comprising:
    a simulated respiratory system, comprising:
      a lung valve;
      a first simulated lung in communication with the lung valve; and
      a breathing pump including a cylinder and a piston dividing the cylinder into first and second chambers, the first chamber being in communication with the lung valve via at least a first flow path, and the second chamber being in communication with the lung valve via at least a second flow path; and
    a simulated airway system configured to be in communication with the second chamber of the breathing pump via at least a third flow path;
  wherein simulating, using the patient simulator, the human patient's breathing pattern comprises reciprocating the piston within the cylinder.

12. The method of claim 11, further comprising actuating an airway valve of the patient simulator to an airway configuration, the airway valve including a first port in communication with the second chamber of the breathing pump, a second port, and a third port in communication with the simulated airway system;
  wherein, when the airway valve is in the airway configuration, the first port is in communication with the third port, but not the second port, so that the first and third ports form part of the third flow path.

13. The method of claim 12, further comprising simulating, using the patient simulator, respiratory distress within the human patient;
   wherein the second port of the airway valve is in communication with an abdominal expansion bag of the patient simulator; and
   wherein simulating, using the patient simulator, respiratory distress within the human patient comprises:
      stroking, when the airway valve is in the abdominal configuration, the piston in a first direction to produce a pressure decrease in the abdominal expansion bag and force air from the first chamber of the breathing pump into the first simulated lung via at least the first flow path; and
      stroking, when the airway valve is in the abdominal configuration, the piston in a second direction, which is opposite the first direction, to produce a pressure increase in the abdominal expansion bag and draw air out of the first simulated lung and into the first chamber of the breathing pump via at least the first flow path.

14. The method of claim 11, wherein the lung valve includes first, second, and third ports, the first chamber of the breathing pump being in communication with the first port via at least the first flow path, the first simulated lung being in communication with the second port, and the second chamber of the breathing pump being in communication with the third port via at least the second flow path; and
   wherein the method further comprises actuating the lung valve between a spontaneous breathing configuration, in which the first port is in communication with the second port, and an assisted breathing configuration, in which both of the first and third ports are in communication with the second port.

15. The method of claim 14, wherein the lung valve further includes a fourth port arranged so that, in the spontaneous breathing configuration, the first port is in communication with one, or both, of the second port and the fourth port, and, in the assisted breathing configuration, both of the first and third ports are in communication with one, or both, of the second and fourth ports; and
   wherein the simulated respiratory system further comprises a second simulated lung in communication with the fourth port.

16. The method of claim 14, wherein at least respective portions of the second and third flow paths are in communication with each other and the second chamber of the breathing pump.

17. The method of claim 14, wherein simulating, using the patient simulator, the human patient's breathing pattern comprises:
   stroking, when lung valve is in the spontaneous breathing configuration and the simulated airway system is in communication with the second chamber of the breathing pump via at least the third flow path, the piston in a first direction to force air from the first chamber of the breathing pump into the first simulated lung via at least the first flow path, and produce a pressure decrease in the airway system to simulate inhalation of the human patient's breath; and
   stroking, when lung valve is in the spontaneous breathing configuration and the simulated airway system is in communication with the second chamber of the breathing pump via at least the third flow path, the piston in a second direction, which is opposite the first direction, to draw air out of the first simulated lung into the first chamber of the breathing pump via at least the first flow path, and produces a pressure increase in the airway system to simulate exhalation of the human patient's breath.

18. The method of claim 14, further comprising producing, using the patient simulator, a pressure fluctuation in the airway system to simulate the human patient gasping for breath;
   wherein producing, using the patient simulator, the pressure fluctuation in the airway system to simulate the human patient gasping for breath comprises:
      stroking the piston in a first direction to produce a pressure decrease in the airway system while permitting air to escape from the third port of the lung valve to the airway system via at least respective portions of the second and third flow paths; and
      stroking the piston in a second direction, which is opposite the first direction, to produce a pressure increase in the airway system while permitting air to escape from the airway system to the third port of the lung valve via at least respective portions of the second and third flow paths.

19. The method of claim 18, wherein at least a portion of the second flow path is smaller in diameter than the first flow path to facilitate said pressure fluctuation.

20. The method of claim 18, further comprising operably coupling a mechanical ventilator to the simulated airway system, the mechanical ventilator being configurable to sense said pressure fluctuation.

* * * * *